United States Patent
Ryu et al.

(10) Patent No.: US 7,476,780 B2
(45) Date of Patent: Jan. 13, 2009

(54) ROOT AGROINOCULATION METHOD FOR VIRUS INDUCED GENE SILENCING

(75) Inventors: Choong-Min Ryu, Yusong Tae-Jon (KR); Kirankumar S. Mysore, Ardmore, OK (US)

(73) Assignee: The Samuel Roberts Noble Foundation, Ardmore, OK (US)

( * ) Notice: Subject to any disclaimer, the term of this patent is extended or adjusted under 35 U.S.C. 154(b) by 340 days.

(21) Appl. No.: 11/107,370

(22) Filed: Apr. 15, 2005

(65) Prior Publication Data
US 2006/0037105 A1 Feb. 16, 2006

Related U.S. Application Data

(60) Provisional application No. 60/562,833, filed on Apr. 16, 2004.

(51) Int. Cl.
*C12N 15/82* (2006.01)
*C12N 15/84* (2006.01)

(52) U.S. Cl. .................. 800/285; 800/279; 800/286; 800/294

(58) Field of Classification Search ................. None
See application file for complete search history.

(56) References Cited

OTHER PUBLICATIONS

Abbink et al., "Silencing of a gene encoding a protein component of the oxygen-evolving complex of photosystem II enhances virus replication in plants," *Virology*, 295:307-319, 2002.
Baulcombe, "RNA silencing," *Current Biol.*, 12:R82-R84, 2002.
Baulcombe, "Viruses and gene silencing in plants," *Arch. Virol.*, (15):189-201, 1999.
Burger et al., "Virus-induced silencing of sterol biosynthetic genes: identification of a *Nicotiana tabacum* 1. obtusifoliol-14α-demethylase (CYP51) by genetic manipulation of the sterol biosynthetic pathway in *Nicotiana benthamiana* l.," *J. Exp. Bot.*, 54:1675-1683, 2003.
Burton et al., "Virus-induced silencing of a plant cellulose synthase gene," *Plant Cell*, 12(5):691-706, 2000.
Dinesh-Kumar et al., "Virus-induced gene silencing," In: *Plant Functional Genomics*, Grotewold (Ed.), Humana Press, Inc., Totowa, NJ, 236:287-293, 2003.
Ekengren et al., "Two mapk cascades, npr1, and tga transcription factors play a role in pto-mediated disease resistance in tomato," *Plant J.*, 36:905-917, 2003.
Escobar and Dandekar, "*Agrobacterium tumefaciens* as an agent of disease," *Trends Plant Sci.*, 8, 380-386, 2003.
Evans and Jeske, "Complementation and recombination between mutants of complementary sense genes of dna a of abutilon mosaic virus," *Virology*, 197:492-496, 1993.
Goodwin et al., "Genetic and biochemical dissection of transgenic rna-mediated virus resistance," *Plant Cell*, 8, 95-105, 1996.
Gosselé et al., "SVISS—a novel transient gene silencing system for gene function discovery and validation in tobacco plants," *Plant J.*, 32:859-866, 2002.
Guo and Garcia, "Delayed resistance to plum pox potyvirus mediated by a mutated rna replicase gene: involvement of a gene-silencing mechanism," *Mol. Plant-Microbe Interact.*, 10,160-170, 1997.
Hanley-Bowdoin et al., "Transient expression of heterologous mas using tomato golden mosaic virus," *Nucleic Acids Res.*, 16:10511-10528, 1988.
Hiriart et al., "Dynamics of the vigs-mediated chimeric silencing of the *Nicotiana benthamiana* Ch1H gene and of the tobacco mosaic virus vector," *Mol. Plant-Microbe Interact.*, 16:99-106, 2003.
Hiriart et al., "Suppression of a key gene involved in chlorophyll biosynthesis by means of virus-inducing gene silencing," *Plant Mol. Biol.*, 50:213-224, 2002.
Kumagai et al., "Cytoplasmic inhibition of carotenoid biosynthesis with virus-derived ma," *Proc. Natl. Acad. Sci.* USA, 92,1679-1 683, 1995.
Lindbo et al., "Induction of a highly specific antiviral state in transgenic plants: implications for regulation of gene expression and virus resistance," *Plant Cell* 5, 1749-1 759, 1993.
Liu et al., "Tobacco *rar1*, *eds1* and *npr1/nim1* like genes are required for *n*-mediated resistance to tobacco mosaic virus," *Plant J.*, 30:415-429, 2002.
Liu et al., "Virus-induced gene silencing in tomato," *Plant J.*, 31:777-786, 2002.
Lu et al., "High throughput virus-induced gene silencing implicates heat shock protein 90 in plant disease resistance," *EMBO J.*, 22:5690-5699, 2003.
Lu et al., "Virus-induced gene silencing in plants," *Methods*, 30:296-303, 2003.
MacFarlane and Popovich, "Efficient expression of foreign proteins in roots from tobravirus vectors," *Virology*, 267:29-35, 2000.

(Continued)

*Primary Examiner*—Ashwin Mehta
(74) *Attorney, Agent, or Firm*—Sonnenschein Nath & Rosenthal LLP

(57) ABSTRACT

The invention provides novel methods and compositions for modulating gene function in plants. In particular, the invention provides methods and compositions that allow efficient induction of virus-induced gene silencing in plants. The invention is significant in that it allows high throughput analysis of gene function in plants.

33 Claims, 13 Drawing Sheets

OTHER PUBLICATIONS

Peart et al., "Ubiquitin ligase-associated protein sgt1 is required for host and nonhost disease resistance in plants," *Proc. Natl. Acad. Sci. USA*, 99:10865-10869, 2002.

Peele et al., "Silencing of meristematic gene using geminivirus-derived vectors," *Plant J.*, 27(4):357-366, 2001.

Pruss et al., "Plant viral synergism: the potyviral genome encodes a broad-range pathogenicity enhancer that transactivates replication of heterologous viruses," *Plant Cell*, 9:859-868, 1997.

Ratcliff et al., "Tobacco rattle virus as a vector for analysis of gene function by silencing," *Plant J.*, 25:237-245, 2001.

Rochester et al., "Systematic movement and symptom production following agroinoculation with a single dna of tomato yellow leaf curl geminivirus (Thailand)," *Virology*, 178:520-526, 1990.

Ruiz et al., "Initiation and maintenance of virus-induced gene silencing," *Plant Cell*, 10:937-946, 1998.

Ryu et al., "Agrodrench: a novel and effective agroinoculation method for virus-induced gene silencing in roots and diverse solanaceous species," *The Plant Journal*, 2001, vol. 40, p. 322-331.

Saedler and Baldwin, "Virus-induced gene silencing of jasmonate-induced direct defences, nicotine and trypsin proteinase-inhibitors in *Nicotiana attenuata*," *J. Exp. Bot.*, 55:151-157, 2003.

Sharma et al., "Virus-induced silencing of wipk and *sipk* genes reduced resistance to a bacterial pathogen, but has no effect on the infl-induced hypersensitive response (HR) in *Nicotiana benthamiana*," *Mol. Genet. Genomics*, 269:583-591, 2003.

Smith et al, "Transgenic plant virus resistance mediated by untranslatable sense rnas: expression, regulation, and fate of nonessential rnas," *Plant Cell*, 6, 1441-1453, 1994.

Tzfira and Citovsky., "The agrobacterium-plant cell interaction," *Plant Physiology*, 133:943-947, 2003.

Vance and Vaucheret, "RNA silencing in plants-defense and counterdefense," *Science*, 292(5525):2277-2280, 2001.

Vellios et al., "Immunogold localization of tobravirus 2b nematode transmission helper protein associated with virus particles," *Virology*, 300:118-124, 2002.

Visser and Bol, "Nonstructural proteins of *tobacco rattle virus* which have a role in nematode-transmission: expression pattern and interaction with coate protein," *J. Gen. Virol.*, 80:3273-3280, 1999.

Visser et al., "Nematode transmission of tobacco rattle virus serves as a bottleneck to clear the virus population from defective interferring rnas," *Virology*, 263:155-165, 1999.

Voinnet, "RNA silencing as a plant immune system against viruses," *Trends Genet.*, 17:449-459, 2001.

Yoshioka et al., "*Nicotiana benthamian* gp91*phox* homologs *NbrbohA* and *NbrbohB* participate in $H_2O_2$ accumulation and resistance to *Phytophthora infestans*," *Plant Cell*, 15:706-718, 2003.

Anand et al., "SGT, Skp and Rar of the E3 Ubiquitin ligase pathway are required for the integration of the T-DNA into the plant genome," Plant Biology Division meeting, Samuel Roberts Noble Foundation, Ardmore, OK, Aug. 17, 2004.

Holzberg et al., "Barley strip mosaic virus-induced gene silencing in a monocot plant," *The Plant Journal*, 30(3):315-327, 2002.

Ryu et al., "Agrodrench: a simple and efficient method of agroinoculation for virus induced gene silencing in solanaceae," Plant Biology Division meeting, Samuel Roberts Noble Foundation, Ardmore, OK, undated.

Ryu et al., "Attenuation of crown gall formation by systemic acquired resistance," Plant Biology Division meeting, Samuel Roberts Noble Foundation, Ardmore, OK, Aug. 17, 2004.

ROOT AGROINOCULATION METHOD FOR VIRUS INDUCED GENE SILENCING

This application claims the priority of U.S. Provisional Patent Application Ser. No. 60/562,833, filed Apr. 16, 2004, the entire disclosure of which is specifically incorporated herein by reference.

BACKGROUND OF THE INVENTION

1. Field of the Invention

The invention relates generally to the field of molecular biology. More specifically, it relates to compositions and methods for modulating and analyzing gene function in plants.

2. Description of the Related Art

Several technologies have been used to determine plant gene function in vivo. For example, classical breeding of cultivars allows the genetic mapping of various genes. Mutagenesis of plants followed by analysis of progeny identifies gene function through loss of specific phenotypes. Transformation of plants with sequences of unknown function followed by phenotype analysis of progeny is another example of a technology used by research scientists to determine gene function. However, these techniques require a large amount of time to obtain results.

Recently, a new procedure for identifying gene function in plants has appeared and captured the interests of many plant scientists. This procedure utilizes plant viruses to express a small portion of host genes with unknown functions in the infected plant. The replication of the virus vector induces a host surveillance system that will knock out expression of genes with identity to the transiently expressed sequence through the mechanism known as virus-induced gene silencing (VIGS) (Baulcombe, 1999; Vance and Vautheret, 2001). To date, several viruses (e.g., Potato virus X, PVX, Tobacco rattle virus, TRV, Tobacco mosaic virus, TMV and Tomato golden mosaic virus, TGMV) have been successfully used as vectors for VIGS in several dicotyledonous plants (Kumagai et al., 1995; Ruiz et al., 1998; Burton et al., 2000; Peele et al., 2001; Ratcliff et al., 2001; Liu, 2002; Hiriart et al., 2002) and one virus, Barley stripe mosaic virus (BSMV), in a monocotyledonous plant (barley) (Holzberg et al., 2002).

VIGS occurs in plants when there is sequence similarity between the virus sequence and a plant gene sequence, either native or transgenic (Lindbo et al., 1993; Kumagai et al., 1995). It has been indicated that the mechanism involved is post-transcriptional and targets RNA molecules in a sequence-specific manner (Smith et al., 1994; Goodwin et al., 1996; Guo and Garcia, 1997). Observations that viruses can both cause and be the targets of gene silencing have suggested that the mechanism is associated with anti-viral plant defense mechanisms (Pruss et al., 1997). Gene silencing can be activated in virally infected plants when part of a gene or its RNA is perceived as part of a virus genome or transcript. This can be achieved by including a portion or all of a plant gene sequence in a viral transcript.

While the foregoing studies have furthered the ability to use VIGS for analysis of plant gene function, the effectiveness of the technique has still been limited. The efficiency in delivery of VIGS vectors to plants of a number of different species in particular has been troublesome. In order to allow the analysis of large numbers of genes, efficient methods for the high-throughput analysis of plant gene function are needed. Such techniques would allow use of high-throughput VIGS for genome-wide identification of gene function where not previously possible.

SUMMARY OF THE INVENTION

In one aspect, the invention provides a method of inhibiting the expression of a plant gene in a plant comprising the steps of: a) obtaining a solution comprising recombinant *Agrobacterium tumefaciens* comprising a heterologous nucleic acid sequence complementary to a target plant gene or the complement thereof and a nucleic acid sequence of a virus that is capable of inducing silencing of the target plant gene; and b) contacting roots of the plant with the solution, wherein the expression of the target gene is inhibited in the plant. In certain embodiments of the invention, the heterologous nucleic acid sequence may be in sense and/or antisense orientation relative to a promoter sequence. In the method, contacting the roots with the solution may be carried out, for example, from about 1 to about 3 weeks of age. In certain embodiments, the heterologous nucleic acid sequence may comprise at least 17, 25, 50, 75, 125 or more nucleotides complementary to the target plant gene. The heterologous nucleic acid sequence may also comprise a cDNA from the target plant gene or a fragment thereof.

In certain embodiments, a plant used with the invention is a dicotyledonous plant, including a tobacco, tomato, soybean, alfalfa, cotton, peanut, or pea plant. The plant may also be a member of the family Solenaceae, including tomato, pepper or tobacco. The plant may also be a monocotyledonous plant, for example, wheat, maize, rye, rice, oat, barley, turfgrass, sorghum, millet or sugarcane. The plant may be in a growth media, including soil or agar. Contacting the roots may comprise applying the solution to the growth media. Expression of the target gene may be inhibited in the roots of the plant, or in aerial parts such as leaves or stems of the plant.

In another aspect, the invention provides a method of identifying the function of a plant gene comprising the steps of: a) obtaining a solution comprising recombinant *Agrobacterium tumefaciens* comprising a heterologous nucleic acid sequence complementary to a plant gene or the complement thereof and a nucleic acid sequence of a virus that is capable of inducing silencing of the plant gene; and b) contacting the roots of a plant with the solution, wherein the expression of the plant gene is inhibited in the plant; and c) identifying an altered phenotype associated with the plant gene based on a difference in the phenotype of the plant relative to a corresponding plant which has not been contacted with the solution. In certain embodiments, step b) is performed on a population of plants. In one embodiment, step b) comprises a population of recombinant *Agrobacterium tumefaciens* comprising a plurality of heterologous nucleic acid sequences. The plant may be, for example, a monocotyledonous plant such as rice or other plant. The plant may also be a dicotyledonous plant, including a member of the family Solenaceae, and may be tomato, pepper or tobacco. In certain embodiments the virus may be tobacco rattle virus or Potato virus X (PVX). Identifying an altered phenotype may comprise any desired method, including a chemical assay or visual observation. The expression of the plant gene may be inhibited in any plant part, including roots, leaves and/or stems of the plant.

In yet another aspect, the invention provides a high-throughput method for identifying the function of plant genes comprising the steps of: a) obtaining: i) a plurality of solutions each comprising recombinant *Agrobacterium tumefaciens* comprising a heterologous nucleic acid sequence complementary to a plant gene or the complement thereof and a nucleic acid sequence of a virus that is capable of inducing silencing in the plant, wherein the recombinant *Agrobacterium tumefaciens* collectively comprise heterologous nucleic acid sequences complementary to a plurality of plant genes or the complements thereof; and ii) a population of plants the roots of which are comprised in a growth media; b) contacting the roots of the population of plants with the solutions, wherein the expression of at least one gene from the plurality of plant genes is inhibited in the population of plants; and c) identifying the function of at least one member of the plurality of plant genes based on a change in the phenotype of at least one plant contacted with the recombinant *Agrobacterium tumefaciens* relative to a plant that has not been contacted with the recombinant *Agrobacterium tumefaciens*.

BRIEF DESCRIPTION OF THE DRAWINGS

The following drawings form part of the present specification and are included to further demonstrate certain aspects of the invention. The invention may be better understood by reference to one or more of these drawings in combination with the detailed description of specific embodiments presented herein.

FIG. 3A, Suppression of GFP expression in the roots of *N. benthamiana* 16C plants. GFP fluorescence in roots was observed under confocal microscope 14 days after infection with TRV2-GFP or TRV2-00 (empty vector) by agrodrench or leaf infiltration. FIG. 3B, Suppression of Actin gene in *N. benthamiana* roots. *N. benthamiana* plants were inoculated with *Agrobacterium* containing TRV2-Actin or TRV2-00 (empty vector) either by agrodrench or leaf infiltration method. Photograph was taken 14 days after inoculation. FIG. 3C, VIGS mediated degradation of specific RNA transcripts in *N. benthamiana* roots. Total RNA was isolated from roots of the plants silenced for the genes shown on the right, either by leaf infiltration or agrodrench method, and was used to generate first-strand cDNA. RNA from plants inoculated with TRV alone was used as a vector control. The cDNA was used for RT-PCR reaction using primers specific to the targeted gene (see Table 1). PCR products were sampled from each PCR cycle number indicated at the bottom and were separated on an agarose gel and stained with ethidium bromide. Rectangular boxes emphasize the difference in transcript accumulation observed between agrodrench and leaf infiltration methods of VIGS. The amount of elongation factor-1 alpha (EF1 α) transcripts was determined for every gene-silenced plant as a control and similar results were obtained. The results indicate that the agrodrench method of gene silencing is more effective in degrading specific transcripts when compared to the leaf infiltration method.

FIG. 4A, PDS and PB7 silencing in *N. benthamiana*, tomato, tobacco and pepper. Plants were inoculated with *Agrobacterium* containing either TRV2-PDS or TRV2-PB7 by agrodrench method. Photograph was taken 21 days after inoculation. FIG. 4B, Degradation of PDS transcripts during gene silencing in various *Solanaceae* species. Total RNA was isolated from leaves of the various plants silenced for PDS, by agrodrench method, and was used to generate first-strand cDNA. RNA from plants inoculated with TRV alone (TRV-00) was used as a control. The cDNA was used for RT-PCR reaction using primers specific to PDS gene (see Table 1). PCR products were sampled from each PCR cycle number indicated at the top and were separated on an agarose gel and stained with ethidium bromide. The amount of elongation factor-1 alpha (EF1 α) transcripts was determined for every gene-silenced plant as a control.

FIG. 5A, Silencing of PDS and Chl H genes in sterile grown *N. benthamiana* seedlings. *N. benthamiana* seeds were surface sterilized and germinated on sterile growth media (see EXAMPLE 1) in 24 well microtiter plates. One week after germination, *Agrobacterium* containing either TRV2-NbPDS or TRV2-NbChl H was applied on to the agar medium along with *Agrobacterium* containing pTRV1. One week after inoculation, photobleaching was observed for PDS silenced plants and yellowing was observed for Chl H silenced plants. FIG. 5B and FIG. 5C, Silencing of PDS and Chl H genes in soil grown *N. benthamiana*, Petunia and pepper seedlings. Seeds were germinated in soil and one week after germination, *Agrobacterium* containing either TRV2-NbPDS or TRV2- NbChl H, along with *Agrobacterium* containing pTRV1, was applied by agrodrench method. One week after inoculation, photobleaching was observed for PDS silenced plants and yellowing was observed for Chl H silenced plants. Photograph was taken 2 weeks after inoculation.

DETAILED DESCRIPTION OF THE INVENTION

Figure 1:
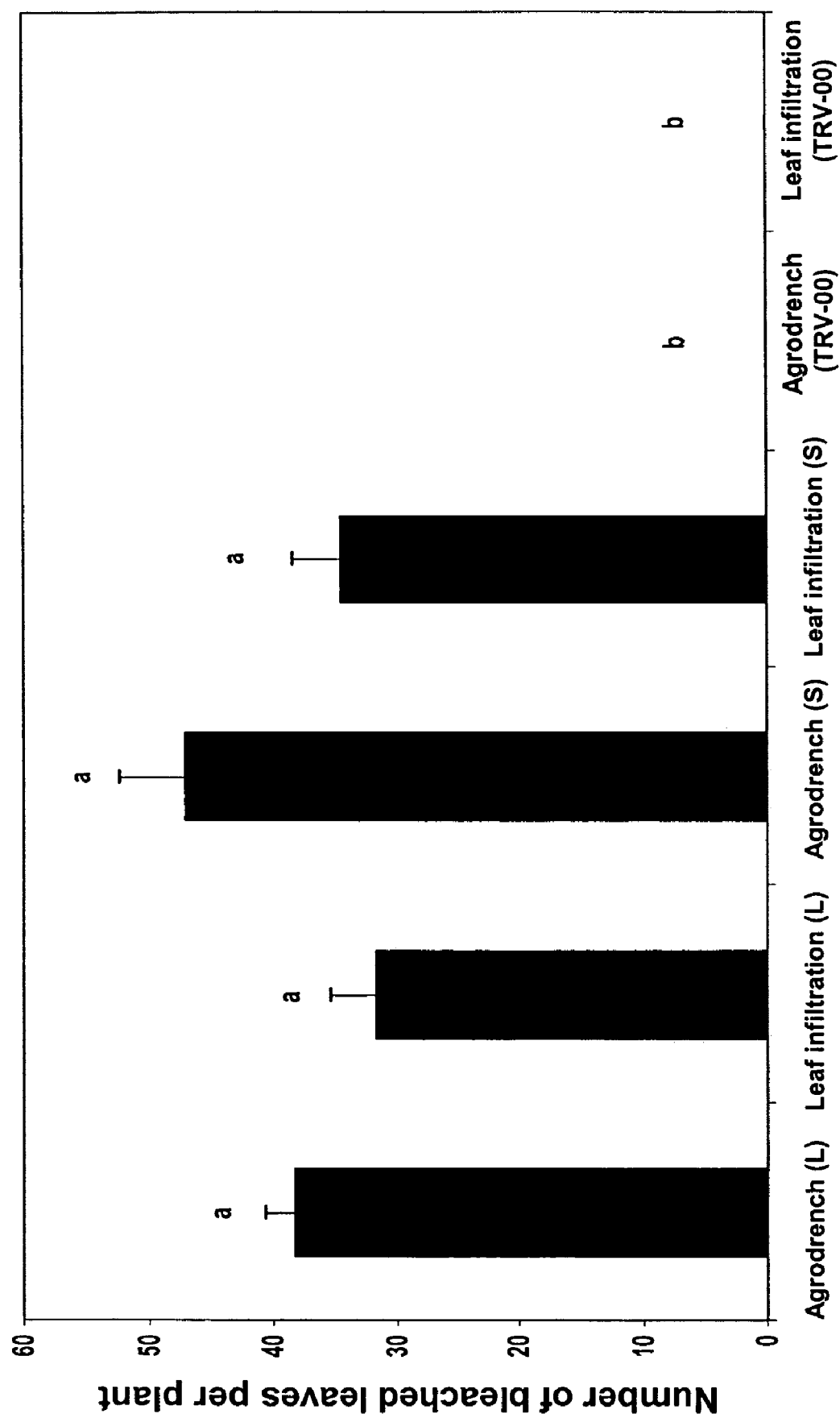
FIG. 1: Development of agrodrench method of agroinoculation. *N. benthamiana* plants were inoculated with *Agrobacterium*, grown on solid medium (S) or liquid medium (L), containing pTRV2 alone (TRV2::00) or TRV2-NbPDS either by agrodrench or leaf infiltration methods. *Agrobacterium* containing pTRV1 was co-inoculated along with *Agrobacterium* containing pTR V2. Number of bleached leaves per plant in each treatment was counted 21 days after TRV inoculation. Letters indicate significant differences using Fisher's LSD test at P=0.05.

The inventors have overcome the limitations of the prior art by providing methods and compositions for the high-throughput analysis of gene function. Virus-induced gene silencing (VIGS) is an extremely powerful tool for functional genomics in plants. The inventors illustrated the technique initially using an *Agrobacterium* binary vector including Tobacco rattle virus (TRV) sequences for VIGS. The inoculation of *Agrobacteria* containing the VIGS vectors was earlier shown to initiate virus infection resulting in RNA silencing in plants. Leaf infiltration has been the most common method of agroinoculation being used for VIGS. This method has limitations since it is laborious for large scale screening, and also because certain plants, including rice and soybean, respond poorly to leaf infiltrations. The inventors therefore developed a novel method of *Agrobacterium* application that involved in certain embodiments drenching growth media with a solution of recombinant *Agrobacterium* in order to infect plants. Suspensions of $10^9$ cfu/ml *Agrobacterium* adjacent to the plant root were shown to allow efficient induction of VIGS.

Using the novel method that was developed, the inventors were able to obtain significant and robust VIGS prototypes for target plant genes. The method was assessed in different Solanaceae plants such as *Nicotiana benthamiana*, pepper, tobacco, tomato, and petunia. The results also indicated that this novel method is a more effective method of agroinoculation than leaf infiltration for VIGS in roots. This method is highly efficient and therefore will open the door to large scale studies of gene function, which were difficult using prior art techniques such as leaf infiltration.

Wounding of a plant at the crown part prior to agrodrench did not have any effect on agroinoculation. Avirulent *Agrobacterium* strain failed to trigger VIGS by agrodrench, indicating agro transformation may be required for agrodrench.

I. VIGS

Among the various defense responses that are induced in many plants against infectious viruses, one that is highly sophisticated is virus-induced gene silencing (VIGS). VIGS is a RNA-mediated post-transcriptional gene silencing mechanism that can protect plants against foreign gene invasion (Baulcombe, 1999). Besides providing utility for better understanding plant defense mechanisms against plant viruses, VIGS has emerged as a functional genomics tool for knocking out gene expression of desired plant genes in some model plants (Peart et al., 2002; Lui et al., 2002a; Holzberg et al., 2002; Ekengren et al., 2003; Yoshioka et al., 2003; Sharma et al., 2003). VIGS is also being used as a forward genetics tool to identify a desired phenotype (Lu et al., 2003a). Plant virus-based vectors carrying plant sequences homologous to the endogenous plant genes trigger gene silencing through a homology-dependent RNA degradation mechanism commonly referred to as RNA silencing. The dsRNA replication intermediate derived from the virus would be processed so that the small interference RNA (siRNA) in the infected cell would correspond to parts of the viral vector genome, including any nonviral insert (Baulcombe, 2002). If the insert is from a host gene, the siRNAs would target the RNase complex to the corresponding host mRNA and the symptoms in the infected plant would reflect the loss of function of the host gene (Voinnet, 2001; Lu et al., 2003b; Burger et al., 2003; Yoshioka et al., 2003; Abbink et al., 2002). In contrast to conventional mutagenesis, VIGS does not alter the gene itself, but rather transiently suppresses the expression of the gene through degradation of MRNA transcripts. Thus, unlike stable transformation, VIGS allows for the study of genes that would otherwise have a lethal phenotype and would fail to be identified in other conventional mutant screens (Lu et al., 2003a).

Among the several viral vector systems used to trigger VIGS, Tobacco rattle virus (TRV) derived vectors are widely used because they produce mild symptoms on the host, and TRV has a wide host range (Ratcliff et al., 2001; Lu et al., 2003a; Dinesh-Kumar et al., 2003; Liu et al., 2002b). TRV, a well characterized soil borne virus, belongs to the genus Tobravirus and is mostly transmitted through the soil by nematodes (Visser and Bol, 1999; Visser et al., 1999). TRV contains a bipartite positive-sense RNA genome (RNA1/RNA2; Matthews, 1991). RNA1 encodes two viral replication proteins, a movement protein and a seed transmission factor. RNA2 encodes the coat protein and a nematode transmission factor (Vellios et al., 2002). Other viral sequences are also known and may find use with the invention. Non-limiting examples of such viruses include Brome mosaic virus (BMV), Tobacco mosaic virus (TMV), Barley stripe mosaic virus (BSMV) Pea early-browning virus (PEBV), and Potato virus X (PVX).

*Agrobacterium tumefaciens* is a soil-borne pathogen that causes neoplastic growth in plants, referred to as 'crown gall', in several dicotyledonous plants by entering mainly through wounds on roots and stem (Agrios, 1997; Burr and Otten, 1999; Escobar and Dandekar, 2003). *Agrobacterium*-based binary vectors have been widely used for delivering viral vectors into plants and this is referred to as agroinoculation (Hanley-Bowdoin et al., 1988; Rochester et al., 1990; Evans and Jeske 1993). Agroinoculation is also extensively used to deliver VIGS vectors into plants for RNA silencing (Liu et al., 2002a; 2002b; Gosselé et al., 2002; Peart et al., 2003). Leaf infiltration is the most common method of agroinoculation used for VIGS (Lu et al., 2003a). However, the leaf infiltration method has some limitations. Leaf infiltration is laborious for large scale screening, and certain plants like soybean and maize are difficult to infiltrate. Leaf infiltration of TRV-based VIGS vectors do not induce efficient gene silencing in many plants including commercially grown varieties of tomato (Liu et al., 2002a; Ekengren et al., 2003). Leaf infiltration also normally requires fully expanded leaves (Ratcliff et al., 2001; Liu et al., 2002a; 2002b). These limitations prevent the efficient use of VIGS technology on some plant species and in all young seedlings.

The present invention provides the development of a novel method of agroinoculation, called "agrodrench", which involves, in one embodiment, drenching the media around the plant crown part with *Agrobacterium* cell suspension carrying the TRV-VIGS vectors. The inventors demonstrated that agrodrench can be used to conduct VIGS in several Solanaceae species and also in very young seedlings. Agrodrench provides several advantages; for example, agrodrench increases the efficacy of VIGS in roots when compared to leaf infiltration method of agroinoculation. Agrodrench provides a simple and an effective agroinoculation technique that can be extensively used by those of skill in the art for infecting a wide range of plants for VIGS.

II. Nucleic Acids for Modulation of Plant Gene Function

One aspect of the current invention involves the use of VIGS vectors for the modulation of plant gene function. Such vectors will generally include viral nucleic acid sequences in conjunction with nucleic acids having homology to a gene of interest. A representative vector or other nucleic acid of the current invention may, for example, be RNA and/or DNA. RNA can readily be created by in vitro transcription as described herein below. RNA may also be copied as a cDNA of a viral RNA. By including one or more nucleic acids having homology to a host gene with the foregoing vectors, gene silencing of the host gene may be achieved.

As indicated above, a modulation of the phenotype conferred by a gene may be obtained in accordance with the invention by administering a recombinant viral nucleic acid sequence containing a second nucleic acid that has homology to the gene of interest. Such a nucleic acid may be present as a sense and/or antisense RNA and/or DNA. In order to achieve inhibition of gene expression, the added nucleic acid will generally be at least 80%, particularly at least 85%, more particularly at least 90%, and preferably at least 95% homologous in sequence to the gene of interest, or the complement thereof through at least 17, 20, 25 or 30 nucleotides of its sequence. Commonly, such sequences will hybridize to the corresponding nucleic acid sequence in the gene of interest under high stringency conditions. As used herein, "hybridization" or "hybridizes" is understood to mean the forming of a double or triple stranded molecule or a molecule with partial double or triple stranded nature. As used herein "stringent condition(s)" or "high stringency" are those conditions that allow hybridization between or within one or more nucleic acid strand(s) containing complementary sequence(s), but precludes hybridization of random sequences. For example, high stringency may be defined as 0.02M to 0.10M NaCl and 50° C. to 70° C. Nucleic acids that are complementary to a gene of interest may, in certain embodiments of the invention, be defined as capable of hybridizing to the gene of interest or complements thereof under specified stringency conditions. Stringent conditions tolerate little, if any, mismatch between a nucleic acid and a target strand. Such conditions are well known to those of ordinary skill in the art, and are preferred for applications requiring high selectivity. Medium stringent conditions may comprise relatively low salt and/or relatively high temperature conditions, such as provided by about 5×SSC, 50% formamide and 42° C.; or alternatively, 5×SSC, 50% formamide and 55° C. It is understood that the temperature and ionic strength of a desired stringency are determined in part by the length of the particular nucleic acid(s), the length and nucleobase content of the target sequence(s), the charge composition of the nucleic acid(s), and to the presence or concentration of formamide, tetramethylammonium chloride or other solvent(s) in a hybridization mixture. It is also understood that compositions and conditions for hybridization are mentioned by way of non-limiting examples only, and that the desired stringency for a particular hybridization reaction in a plant cell is often determined empirically by comparison to one or more positive or negative controls. Depending on the application envisioned it is preferred to employ varying conditions of hybridization to achieve varying degrees of selectivity of a nucleic acid towards a target sequence.

A recombinant vector provided by the invention may or may not therefore include all cis-elements required for vascular movement of the vector or even its cell-to-cell spread. As is understood in the art, it will generally be preferable that a VIGS vector includes all of the elements needed for systemic spread in an organism. In certain embodiments, these elements may be introduced separately. For example, the inventors displayed the ability to introduce TRV1 and TRV2 of Tobacco rattle virus separately both temporally and spatially and achieve efficient VIGS for a target gene. In this manner, modulation of plant gene expression in a collection of plant cells may be more efficiently carried out. Such vectors may, for example, be administered in a solution and may also contain any other desired ingredients including buffers, cis-elements, surfactants, solvents and similar components.

A nucleic acid sequence corresponding to a gene of interest should generally be of sufficient length that it will be unique to the coding sequence. Generally, sequences of at least 17-20 nucleotides will occur only once in most plant genomes. Often results may be optimized by including longer sequences of a sense and/or antisense region of a gene of interest, including at least about 75, 100, 250 and about 500 nucleotides, including the full length of a coding region of the gene whose expression is to be reduced, as well as associated control elements. Depending on the viral vector, there may be size constraints on the length of nucleic acids homologous to the gene of interest that are used. For example, it may be generally preferable that these nucleic acids had a size of less than about 1 kb when TRV vectors were used for VIGS.

Nucleic acids corresponding to a gene of interest may potentially be placed anywhere in a VIGS vector relative to the nucleic acids of the gene(s) of interest. For example, the nucleic acids may be placed in an untranslated region of a viral RNA so that the function of the viral RNA or any polypeptide products translated therefrom is not adversely affected. Benefit may be obtained by including both sense and antisense nucleic acids for a particular gene. It will generally be preferable that the sense and antisense RNA are at least partly complementary to each other, for example, capable of secondary structures such as a stem-loop structure, which may increase the efficiency of gene silencing.

III. Vector Construction

Construction of VIGS vectors for use with the invention will be well known to those of skill in light of the current disclosure. Recombinant constructs preferably comprise restriction endonuclease sites to facilitate vector construction. Particularly useful are unique restriction endonuclease recognition sites. Examples of some restriction sites may be useful in this regard are HindIII, Tth1111, BsmI, KpnI and XhoI. Endonucleases preferentially break the internal phosphodiester bonds of polynucleotide chains. They may be relatively unspecific, cutting polynucleotide bonds regardless of the surrounding nucleotide sequence. However, the endonucleases which cleave only a specific nucleotide sequence are called restriction enzymes. Restriction endonucleases generally internally cleave nucleic acid molecules at specific recognition sites, making breaks within "recognition" sequences that in many, but not all, cases exhibit two-fold symmetry around a given point. Such enzymes typically create double-stranded breaks.

Many of these enzymes make a staggered cleavage, yielding DNA fragments with protruding single-stranded 5' or 3' termini. Such ends are said to be "sticky" or "cohesive" because they will hydrogen bond to complementary 3' or 5' ends. As a result, the end of any DNA fragment produced by an enzyme, such as EcoRI, can anneal with any other fragment produced by that enzyme. This properly allows splicing of foreign genes into plasmids, for example.

Some endonucleases create fragments that have blunt ends, that is, that lack any protruding single strands. An alternative way to create blunt ends is to use a restriction enzyme that leaves overhangs, but to fill in the overhangs with a polymerase, such as klenow, thereby resulting in blunt ends. When DNA has been cleaved with restriction enzymes that cut across both strands at the same position, blunt end ligation can be used to join the fragments directly together. The advantage of this technique is that any pair of ends may be joined together, irrespective of sequence.

Those nucleases that preferentially break off terminal nucleotides are referred to as exonucleases. For example, small deletions can be produced in any DNA molecule by treatment with an exonuclease which starts from each 3' end of the DNA and chews away single strands in a 3' to 5' direction, creating a population of DNA molecules with single-stranded fragments at each end, some containing terminal nucleotides. Similarly, exonucleases that digest DNA from the 5' end or enzymes that remove nucleotides from both strands have often been used. Some exonucleases which may be particularly useful in the present invention include Bal31, S1, and ExoIII. These nucleolytic reactions can be controlled by varying the time of incubation, the temperature, and the enzyme concentration needed to make deletions. Phosphatases and kinases also may be used to control which fragments have ends which can be joined. Examples of useful phosphatases include shrimp alkaline phosphatase and calf intestinal alkaline phosphatase. An example of a useful kinase is T4 polynucleotide kinase.

Once the source DNA sequences and vector sequences have been cleaved and modified to generate appropriate ends they are incubated together with enzymes capable of mediating the ligation of the two DNA molecules. Particularly useful enzymes for this purpose include T4 ligase, *E. coli* ligase, or other similar enzymes. The action of these enzymes results in the sealing of the linear DNA to produce a larger DNA molecule containing the desired fragment (see, for example, U.S. Pat. Nos. 4,237,224; 4,264,731; 4,273,875; 4,322,499 and 4,336,336, which are specifically incorporated herein by reference).

It is to be understood that the termini of the linearized plasmid and the termini of the DNA fragment being inserted must be complementary or blunt in order for the ligation reaction to be successful. Suitable complementary ends can be achieved by choosing appropriate restriction endonucleases (i.e., if the fragment is produced by the same restriction endonuclease or one that generates the same overhang as that used to linearize the plasmid, then the termini of both molecules will be complementary). As discussed previously, in one embodiment of the invention, at least two classes of the vectors used in the present invention are adapted to receive the foreign oligonucleotide fragments in only one orientation. After joining the DNA segment to the vector, the resulting hybrid DNA can then be selected from among the large population of clones or libraries.

Once a DNA vector has been prepared, it will be readily understood to those of skill in the art that infective RNA transcripts may be made therefrom. For example, commercial kits are available for production of RNA transcripts. One example of such a kit that was used is the mMeSSAGE mMACHINE transcription kit from Ambion (Austin, Tex.).

IV. Assays of Gene Function or Expression

For the determination of gene function, it will generally be desired to infect a plant or part thereof with *Agrobacterium* as described herein comprising a vector carrying a sequence complementary at least in part to one or more gene(s) of interest and determining any phenotypic change resulting from a decrease in expression of the gene(s) of interest. A phenotypic change may be readily identified by comparison of a plant phenotype before and after being treated as described herein with recombinant viral nucleic acid and/or by comparison with plants of a corresponding genotype which may or may not have received the viral nucleic acids.

The techniques of the invention are amenable to large-scale, high-throughput applications. For example, a plurality of recombinant vectors comprising nucleic acids homologous to a large number of plant gene(s) of unknown function could be used to treat a population of plants. In this way, the function of the corresponding gene(s) may be determined. Such plants may be infected with viral vectors at different stages of development or in different tissues depending upon the gene being assayed.

In certain embodiments of the invention, techniques may be used to assay gene expression and generally, the efficacy of a given gene silencing construct. While this may be carried out by visual observation of a change in plant phenotype, molecular tools may also be used. For example, expression may be evaluated by specifically identifying the nucleic acid or protein products of genes. Assays for the production and identification of specific proteins may make use of physical-chemical, structural, functional, or other properties of the proteins. Unique physical-chemical or structural properties allow the proteins to be separated and identified by electrophoretic procedures, such as native or denaturing gel electrophoresis or isoelectric focusing, or by chromatographic techniques such as ion exchange or gel exclusion chromatography. The unique structures of individual proteins offer opportunities for use of specific antibodies to detect their presence in formats such as an ELISA assay. Combinations of approaches may be employed with even greater specificity such as western blotting in which antibodies are used to locate individual gene products that have been separated by electrophoretic techniques. Additional techniques may be employed to absolutely confirm the identity of the product of interest such as evaluation by amino acid sequencing following purification. Although these are among the most commonly employed, other procedures may be additionally used.

Frequently, the expression of a gene product may be determined by evaluating the phenotypic results of its expression. These assays also may take many forms including but not limited to, analyzing changes in the chemical composition, morphology, or physiological properties of the plant. Chemical composition may be altered by expression of genes encoding enzymes or storage proteins which change amino acid composition and may be detected by amino acid analysis, or by enzymes which change compounds that may be analyzed by near infrared reflectance spectrometry. Morphological changes may be observed, such as root growth.

V. Examples

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

EXAMPLE 1

Materials and Methods

A. Plant Material and Growth Conditions

*Nicotiana benthamiana* (both wild-type and 16C transgenic plants expressing GFP), tomato (*Lycopersicon esculentum* cvs. Rutgers and microtom), bell pepper (*Capsicum annum* cv. Marengo), tobacco (*Nicotiana tabacum* cv. Xanthi nc), potato (*Solanum tuberosum* cv. Catalina), Eggplant (*Solanum melongena* cv. Louisiana Long Green), and Petunia (*Petunia hybrida* cv. Freedom Red Star) were used in the experiments listed in below examples. Seeds were germinated in flats with a soil-less potting mixture, BM7 (Berger Co. Quebec, Canada). Two-week-old seedlings were transplanted to 10 cm diameter round pots, containing BM7, with one plant per pot. Fertilizer (20-10-20) along with soluble trace element mix (The Scotts Co. Marysville, Ohio) was applied with water. Greenhouse conditions were kept at 23±3 and 70% humidity under 12 h light. 1-3 week old plants were used for silencing experiments. To obtain sterile *N. benthamiana* plants, seeds were surface-sterilized with 70% ethanol for 1-2 min followed by treatment with 1% sodium hypochlorite for 20 min. Seeds were washed several times with sterile water and was plated on 24 well microtiter plate (one seed/well) containing MS agar (4.32 g/L Murashige and Skoog [MS] minimal slats, 1.5% sucrose, and 1% phytagar) and incubated at 24° C. with 12 h light.

B. Plasmid Construction pTRV1 and pTRV2 VIGS vectors, described in Liu et al., 2002a were obtained from Dr. Dinesh-Kumar, Yale University. A 430-bp pepper PDS fragment was amplified by RT-PCR with primers, pPDSattB1: 5'-ggggacaagtttgtacaaaaaag-caggctGCAATGGAAGGAACATTCGA-3' (SEQ ID NO:1) and pPDSattB2: 5'-ggggacaagtttgtacaaaaaagcag-gctCTTTTCACTGGAGTTGTCCC-3' (SEQ ID NO:2), from common bell pepper. A 451-bp GFP fragment was amplified using primers, gfpattB1: 5'-ggggacaagtttgtacaaaaaagcag-gctCTTTTCACTGGAGTTGTCCC-3' (SEQ ID NO:3) and gfpattB2: 5'-ggggaccactttgtacaa-gaaagctgggtGCTTGTCGGCCATGATGTA-3' (SEQ ID NO:4), from *N. benthamiana* 16C plants. A 365-bp NbChl H gene fragment was amplified by RT-PCR using primers NbChlHattB1: 5'-ggacaagtttgtacaaaaaagcaggctC-GAGCGGCCGCCCGGGCAGGTGGAGATGT-3' (SEQ ID NO:5) and NbChlHattB2: 5'-ggggaccactttgtacaa-gaaagctgggtCATGAATTTGAGCT-TGAAACTTGCCATTGT-3' (SEQ ID NO:6), from *N. benthamiana* plants. The PCR amplified gene fragments were introduced into GATEWAY ready pTRV2 (Liu et al., 2002a) by using GATEWAY cloning system according to manufacturer's recommendations (Invitrogen Co., Carlsbad, Calif.). TRV2-NbActin was obtained from Dr. Rick Nelson, Noble Foundation. TRV2-NbPDS and TRV2-tPDS (Ekengren et al., 2003) were obtained from Dr. Greg Martin, BTI, Cornell University. Sequence of all the pTRV2 derivatives were confirmed by sequencing at the Noble Foundation. Plasmids were introduced into *A. tumefaciens* strain GV2260 by electroporation.

C. RNA Extraction and RT-PCR Analysis

Total RNA from leaf and root tissue were isolated from silenced and non-silenced (infiltrated with empty vector pTRV1 and pTRV2) plants three weeks post inoculation using TRIzol® reagent (Invitrogen Co. Carlsbad, Calif.) according to manufacturer's manuals and treated with RNase-free DNase. A reverse transcriptase (RT) reaction was performed on 1-5 μg of total RNA with 200 units of super-script™ RNase H-reverse transcriptase (Invitrogen Co.), 500 ng oligo $d(T)_{12-16mer}$ primer and 500 μM dNTPs in a final volume of 20 μl. Semi-quantitative PCR was performed in a final volume of 75 μl using 1.5 μl of cDNA, 1×PCR buffer (with 1.5 mM $MgCl_2$), 200 μM dNTP, 200 nM of each pair of gene specific primers and 1.5 units of Go-Taq polymerase (Promega Co. Madison, Wis.). To ensure that only host genes and not the viral RNA transcripts were amplified, the RT transcriptase reactions were performed using oligo d(T) primers. As a loading control for silenced and non-silenced plants, parallel reactions using elongation factor 1-α primers were carried out. The details of all the primers employed for the RT-PCR reactions are detailed in Table 1. PCR conditions used for all the genes, except for GFP amplification, were subject to initial denaturation at 94° C. for 30 sec, annealing at 52° C. for 45 sec, and elongation for 1 min at 72° C. for 40 cycles. Conditions for GFP amplification were as follows, a first cycle of 4 minutes at 94° C., 30 seconds at 59° C. and 30 seconds at 72° C. was followed by 30 seconds at 92° C., 30 seconds at 59° C. and 30 seconds at 72° C. for 39 more cycles. A 10-μl aliquot was removed from each reaction after 20, 25, 30, 35 and 40 cycles. The aliquots were analyzed on a 1.2% agarose gel stained with ethidium bromide. Produce sizes were determined by comparison to a 1 kb DNA ladder (Life Technologies, Rockville, Md.). Images of the RT-PCR ethidium bromide-stained agarose gels were acquired with a CCD camera (Ultra-Lum Inc., Claremont, Calif.). The RT-PCR reactions were repeated twice for three independently silenced and non-silenced plants and similar results were obtained.

TABLE 1

RT-PCR primers used for detecting virus-induced gene silencing for homologous and heterologous genes.

| Primer name | Primer sequences (5'-3') | |
|---|---|---|
| N. benthamiana Actin Forward | CACAGAGCGTGGTTACTCATC | (SEQ ID NO:7) |
| N. benthamiana Actin Reverse | GCAATACCTGGGAACATGGTAG | (SEQ ID NO:8) |
| Pepper PDS Forward | CCTGCAGAAGAGTGGGTATC | (SEQ ID NO:9) |
| Pepper PDS Reverse | GTATAGGAGCTTGTCCCCTG | (SEQ ID NO:10) |
| Tomato PDS Forward | GCTCACTGCTCAGTGTG | (SEQ ID NO:11) |
| Tomato PDS Reverse | CGCTTGCTTCCGACAAC | (SEQ ID NO:12) |
| GFP Forward | CTTTTCACTGGAGTTGTCCC | (SEQ ID NO:13) |
| GEP Reverse | GCTTGTCGGCCATGATGTA | (SEQ ID NO:14) |
| N. benthamiana ef1α Forward | TGGTGTCCTCAAGCCTGGTATGGTTGT | (SEQ ID NO:15) |

TABLE 1-continued

RT-PCR primers used for detecting virus-induced gene silencing for homologous and heterologous genes.

| Primer name | Primer sequences (5'-3') |
|---|---|
| N. benthamiana ef1α Reverse | ACGCTTGAGATCCTTAACCGCAACATTCTT (SEQ ID NO:16) |

D. Agrodrench and Leaf Infiltration Methods

The *Agrobacterium tumefaciens* strain GV2260 containing TRV-VIGS vectors was used for VIGS experiments. Bacteria were grown at 28° C. either on Luria-bertani (LB) agar medium or LB broth with appropriate antibiotics. The bacterial cells were harvested either by scraping the bacteria from agar medium (for bacteria grown on solid medium) or by centrifugation (for bacteria grown in liquid medium) and resuspended into Agrobacterium inoculation buffer (10 mM $MgCl_2$, 10 mM MES [pH 5.6], 150 µM acetosyringone) to a final $OD_{600}$ of 1.0 (for both TRV1 and TRV2) and shaken for at least 4 h at room temperature before infiltration.

For leaf infiltration, each *Agrobacterium* strain containing TRV1 and TRV2 vectors were mixed in 1:1 ratio and infiltrated to the leaves of 2-3 weeks old plants with 1 ml needleless syringe. For agrodrench, *Agrobacterium* strains containing TRV1 and TRV2 were individually drenched, 3 ml each, with a 10 ml pipette into crown part of each plant. Accumulation of virus in the freshly grown part of the plant was detected, 2 weeks after inoculation, by PCR with TRV coat protein specific primers 5'-CTGGGTTACTAGCGGCACT-GAATA-3' (SEQ ID NO:17) (forward primer) and 5'-TC-CACCAAACTTAATCCCGAAATAC-3' (SEQ ID NO:18) (reverse primer). Six to ten replications were done for each experiment and the experiment was repeated at least two times.

E. Confocal Microscopy

Seeds of *N. benthamiana* 16C plants stably expressing green fluorescent protein (Ruiz et al., 1998) were obtained from Dr. David Baulcombe and planted as described above. Two weeks after inoculation of plants with *Agrobacterium* by leaf-inoculation and/or agrodrench methods, the *N. benthamiana* roots were examined using a Bio-Rad 1024 ES confocal laser scanning microscope (BioRad, Hercules, Calif.). GFP in living roots was detected by exciting samples with the 488-nm line of the Krypton-Argon laser and capturing the emission at 522 nm. All images were processed using Adobe Photoshop 5.0 L.E. (Adobe Systems Inc., Mountain View, Calif.).

F. Data Analysis

Data were subjected to analysis of variance using JMP software version 4.0.4 (SAS Institute Inc., Cary, N.C.). When a significant F test was obtained at P=0.05, separation of treatment means was accomplished by Fisher's protected least significant difference (LSD).

EXAMPLE 2

Agrodrench is an Effective Agroinoculation Method for VIGS in *N. benthamiana*

Leaf infiltration methods of inoculation have previously been used for VIGS experiments (Lu et al., 2003a). However, while the leaf infiltration method works efficiently in *N. benthamiana*, a popularly used plant for VIGS experiments, it can be a laborious process for large scale VIGS experiments. The inventors thus developed a simple and efficient method of agroinoculation involving, in one embodiment, drenching the plant rhizosphere (crown part of plant) with *Agrobacterium tumefaciens* containing the viral vector within the T-DNA of a binary vector. The Tobacco rattle virus (TRV; bipartite RNA virus; TRV-RNA1 [TRV1] and TRV-RNA2 [TRV2]) was used in certain embodiments of the present invention as a VIGS vector. It has been demonstrated that a TRV based vectors can be used for VIGS in both *N. benthamiana* and a miniature tomato cultivar, referred to as Micro-tom (Ratcliff et al., 2001; Liu et al., 2002a; Liu et al., 2002b).

To test the effectiveness of agrodrench in *N. benthamiana*, a *N. benthamiana* phytoene desaturase (NbPDS) gene was inserted into a TRV2-based VIGS vector (containing a recombinant TRV2 genome within the T-DNA of an *Agrobacterium* strain GV2260 binary vector) by GATEWAY cloning, and this construct was transformed into the disarmed *Agrobacterium* strain GV2260. The PDS gene encodes an enzyme involved in carotenoid biosynthesis, and silencing of this gene results in photobleaching of plant leaves (Kumagai et al., 1995). Freshly grown *Agrobacterium* strains containing TRV1 and TRV2 (containing NbPDS) were induced with acetosyringone and were mixed in a 1:1 ratio and applied directly into the soil adjacent to the crown part of 2-3 week old *N. benthamiana* plants. Photobleaching was observed on the newly developed leaves of *N. benthamiana* plants after 10 days of inoculation. The procedure was optimized by using several *Agrobacterium* (containing TRV2-NbPDS) concentrations and the minimum concentration required to elicit VIGS was found in these studies to be $10^2$ colony forming units (cfu)/ml; however, maximum gene silencing was observed at concentrations greater than $10^8$ cfu/ml. *Agrobacterium* cultures (containing TRV1 and TRV2-NbPDS) grown on solid medium were slightly more efficient in VIGS when compared to liquid grown cultures even though they were not statistically different at p=0.05 (FIG. 1). Presence of the viral transcripts was detected in the photobleached leaves by using RT-PCR.

The efficiency of VIGS by agrodrench was compared with the leaf infiltration method. Efficiency of VIGS was determined by number of plants that show silencing phenotype (photobleaching) after inoculation with TRV2-NbPDS. Both agrodrench and leaf infiltration methods were 100% efficient in inducing VIGS on *N. benthamiana*. Efficacy of VIGS was determined by counting each and every leaf (small and large), including leaves of secondary shoots, that showed photobleaching. The results, shown in FIG. 1, indicate that the agrodrench method was slightly more effective in VIGS than that of the leaf infiltration method of agroinoculation. However, this is especially significant because of the much greater convenience of use of agrodrench. Statistically the number of silenced leaves between the two methods was not significantly different at P=0.05 (FIG. 1). The only observed difference between the two methods was that the appearance of the silencing phenotype was delayed by 3-4 days in agrodrench method when compared to the leaf infiltration method. This finding is in accordance to the hypothesis that the virus may need more time for infecting and moving within the plant from the site of infection (roots) to the upper parts of the plants (leaves).

The possibility that *Agrobacterium* used in agrodrench should be preferably virulent (as opposed to avirulent) to improve the efficacy of agrodrench was also evaluated. Because agrodrench is an unconventional method of agroinoculation, the possibility that a transformation-efficient *Agrobacterium* strain was required for the systemic movement of the virus was evaluated. It might be possible that during the agrodrench process the virus genome can be released into the soil, from dead *Agrobacterium* cells, and this can be somehow taken up by the plant roots. To determine if the *Agrobacterium* transformation was required for the agrodrench method of agroinoculation, the TRV1 and TRV2-NbPDS vectors were transferred into an avirulent *Agrobacterium* strain that does not contain a Ti plasmid and inoculated *N. benthamiana* using the agrodrench method. Three weeks after inoculation no photobleaching was observed on plants infected with the avirulent *Agrobacterium* strain when compared to T-DNA transfer-efficient (virulent) *Agrobacterium* strain GV2260 that showed photobleaching on newly developed leaves. This result suggests that the *Agrobacterium*-mediated T-DNA transformation is required for agrodrench method of agroinoculation.

EXAMPLE 3

Agrodrench is More Effective than the Leaf Infiltration Method of Agroinoculation for VIGS in Roots VIGS is popularly used to transiently knockout genes that show a characteristic phenotype on foliar area (Lu et al., 2003b; Burger et al., 2003; Yoshioka et al., 2003; Abbink et al., 2002; Liu et al., 2002b; Ekengren et al., 2003). TRV-based VIGS was recently shown to be effective in silencing genes in plant roots (Saedler and Baldwin, 2004). TRV is a soil-borne virus transmitted by nematodes and accumulates in high titer in the root system (MacFarlane and Popovich 2000). The inventors hypothesized that root infection with TRV-VIGS vectors would be more effective in silencing genes in roots.

Figure 3A:
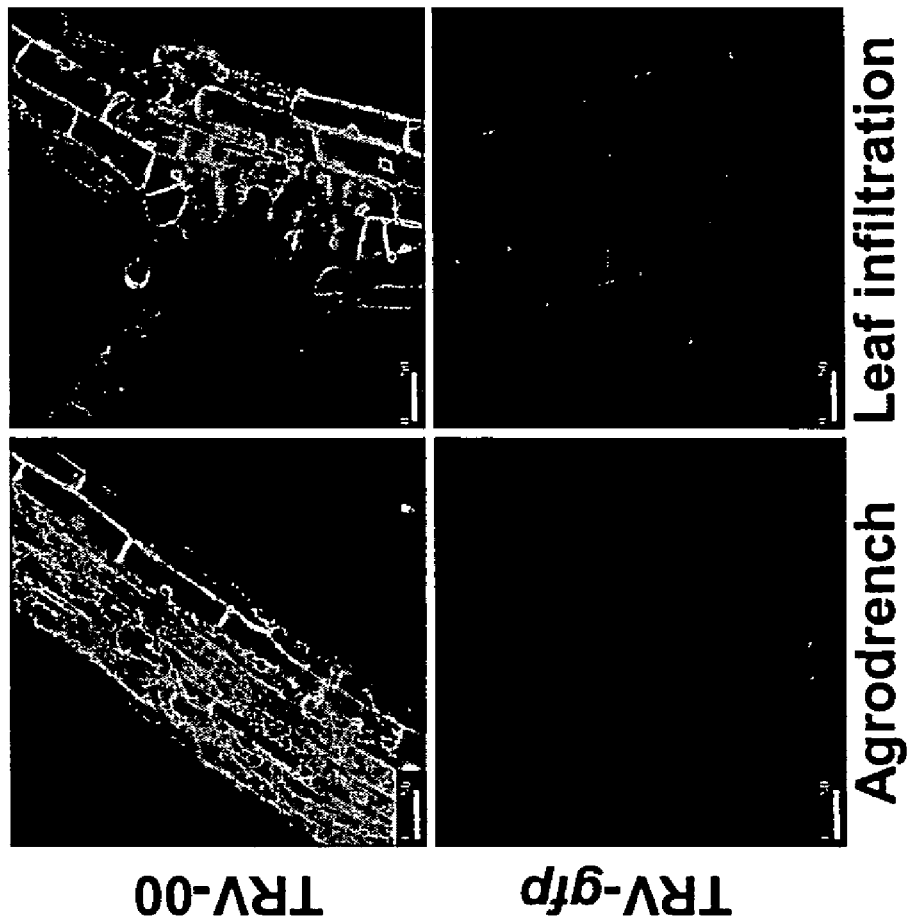
FIGS. 3A-C: RNA silencing in roots by agrodrench method.
Figure 3B:

The leaf infiltration and agrodrench methods of agroinoculation were compared to determine the efficacy of VIGS in plant roots by using green fluorescent protein (GFP), PDS and Actin as indicator genes. NbPDS was PCR amplified from cDNA synthesized from *N. benthamiana* leaf tissue and cloned into TRV2-VIGS vector by GATEWAY cloning. GFP gene was PCR amplified from 16C plant (transgenic *N. benthamiana* plant expressing GFP; Brigneti et al., 1998) and was cloned into TRV2 vector by GATEWAY cloning. TRV-NbActin clone was obtained. *Agrobacteria* containing either TRV2-NbPDS or TRV2-NbActin were inoculated, along with *Agrobacterium* containing TRV1, on to wild-type *N. benthamiana* plants either by leaf infiltration or agrodrench methods. *Agrobacteria* containing TRV2-GFP, along with *Agrobacterium* containing TRV1, were inoculated on to 16C plants (Brigneti et al., 1998) either by leaf infiltration or agrodrench methods. *Agrobacterium* strain containing TRV2-empty vector was used as a control. Gene silencing phenotypes were observed in the roots of TRV2-GFP and TRV2-NbActin inoculated plants 14 days after inoculation (FIG. 3A and FIG. 3B). Silencing of the Actin gene resulted in severely stunted shoot and roots and silencing of GFP gene, in 16C plants, resulted in loss of green fluorescence under UV light. Interestingly, agrodrench method resulted in a more severe phenotype (indicating an increased gene silencing effect) when compared to the leaf infiltration method. It was indicated that the virus accumulation in the roots following the root transformation that occurred during agrodrench contributes to a more rapid and effective VIGS in roots contrary to the leaf infiltration method where the virus or the gene silencing signal (Ruiz et al., 1998; Guo and Ding 2002) has to move from the leaves to the root to trigger gene silencing.

Figure 3C:
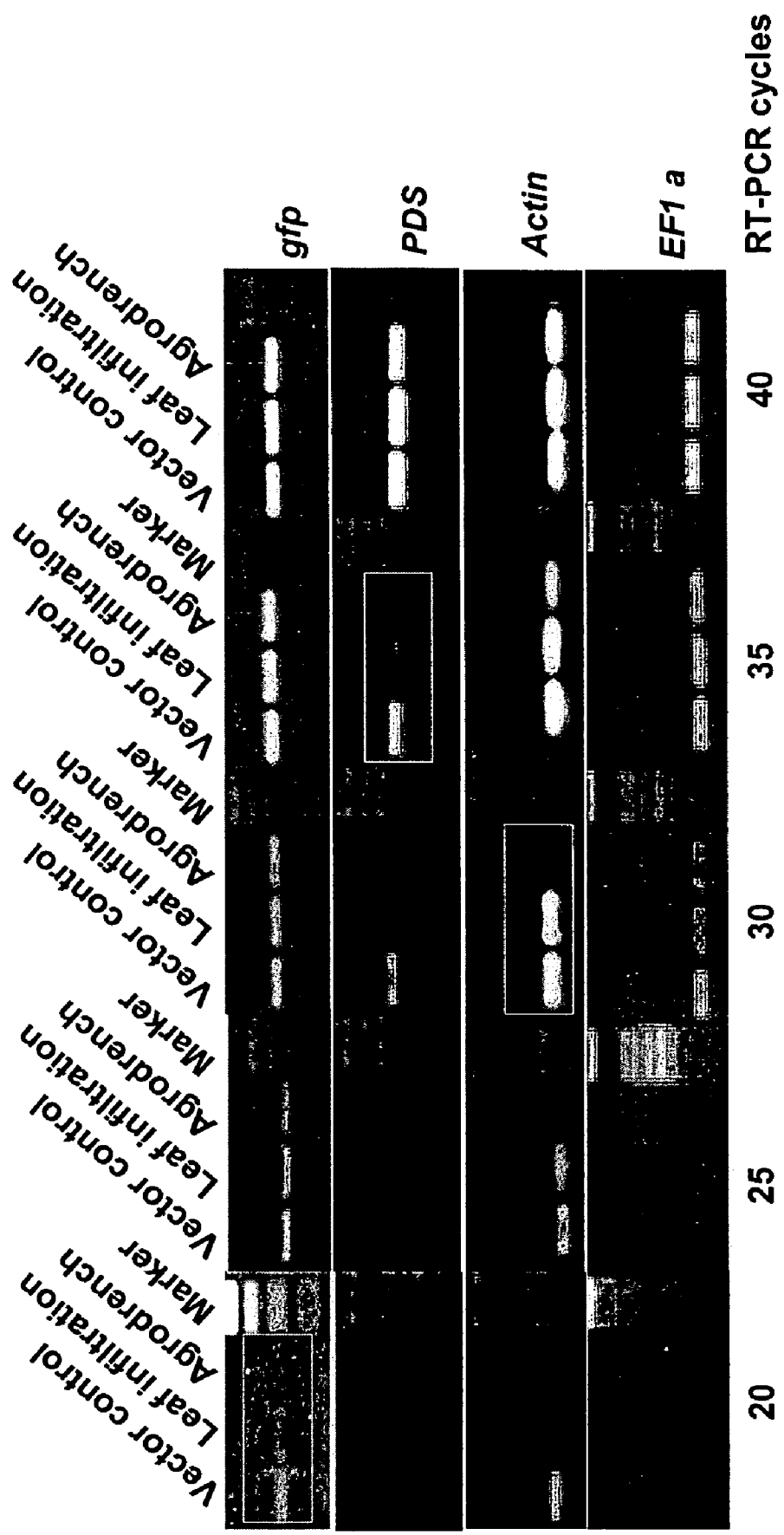

To further confirm the gene silencing at the molecular level, semi-quantitative RT-PCR analyses were performed to quantify the transcript levels of the silenced endogenous genes (FIG. 3C). RNA was isolated, 14 days after inoculation, from roots of TRV2-NbPDS, TRV2-GFP, TRV2-NbActin and TRV2-empty vector inoculated plants. Gene-specific primers (Table 1) for NbPDS, GFP and NbActin were used to amplify the cDNA of the respective genes using RT-PCR (reverse transcription PCR). Suppression of PDS and GFP transcripts was slightly more effective using agrodrench method of VIGS when compared to leaf infiltration (FIG. 3C). Surprisingly, suppression of Actin transcripts was very strong by agrodrench method and this correlated very well with the plant phenotype (FIG. 3B and FIG. 3C). These findings could very well open up a whole new area for functional characterization of genes expressed in roots that are involved in diverse biological functions (physiological, biochemical and plant-microbe interactions).

EXAMPLE 4

Agrodrench is Effective for VIGS in Various Plant Species within the Solanaceae Family

Figure 4A:
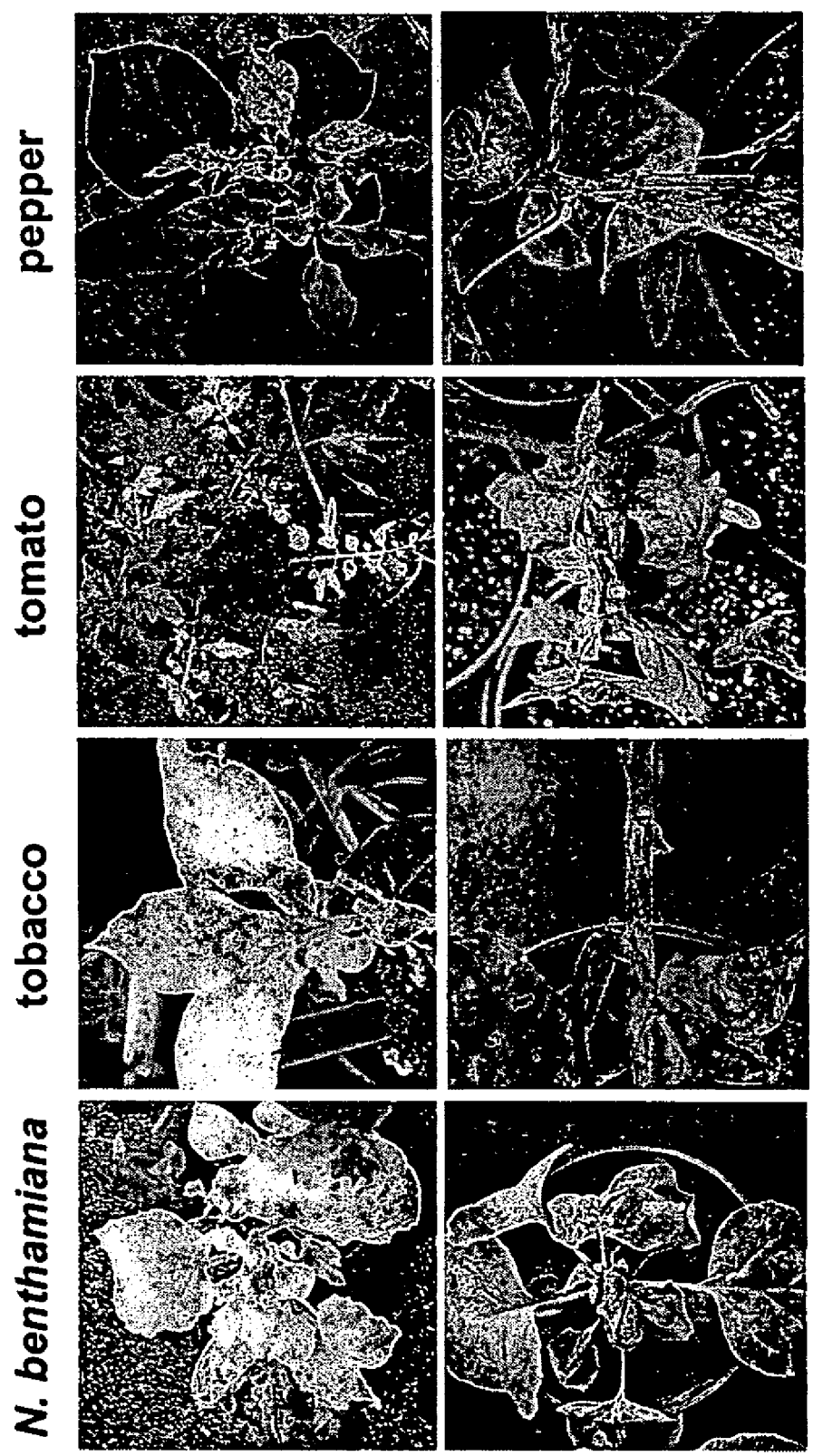
FIGS. 4A-B: Application of agrodrench method for VIGS in different *Solanaceae* species.
Figure 4B:
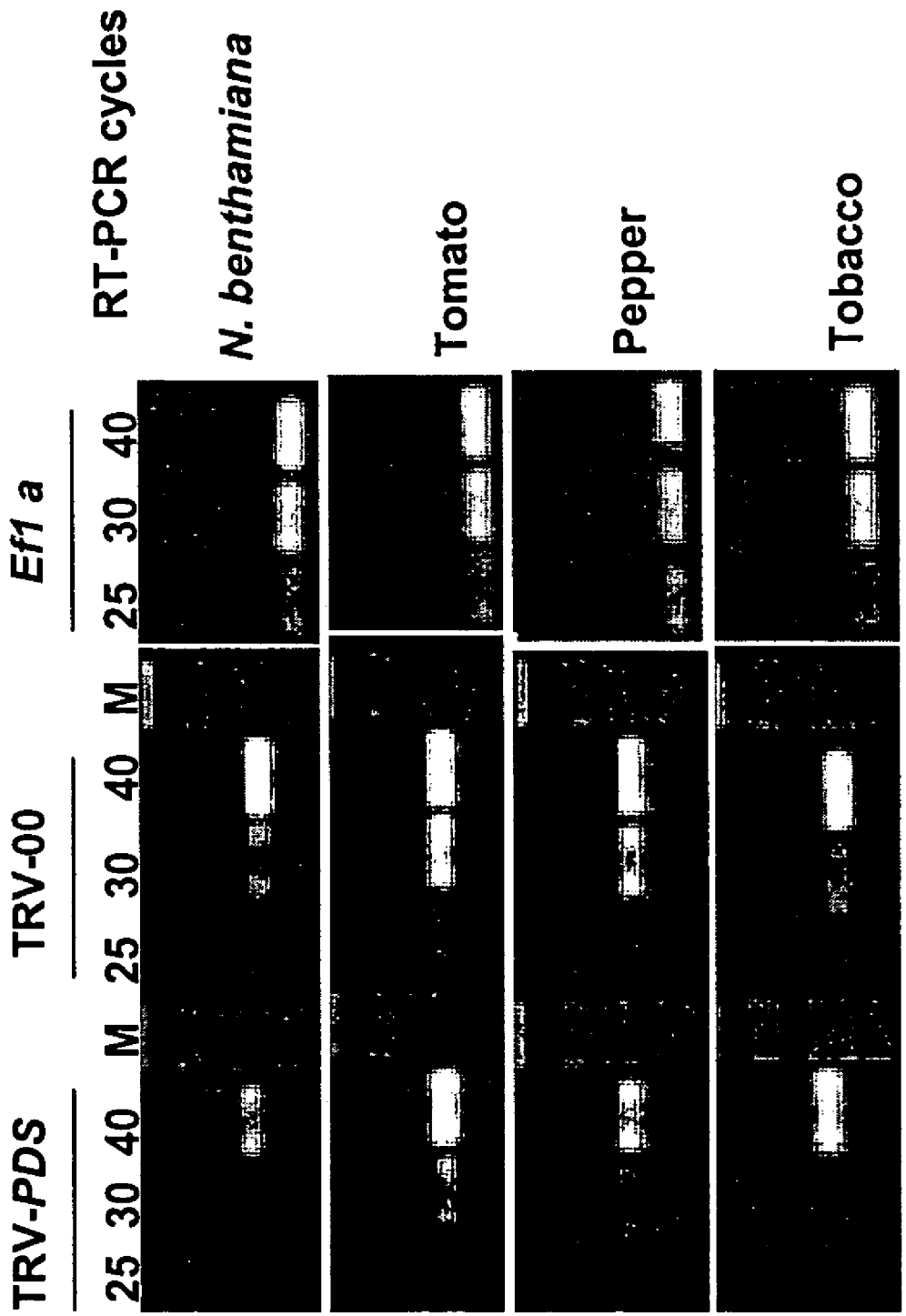
Figure 5A:
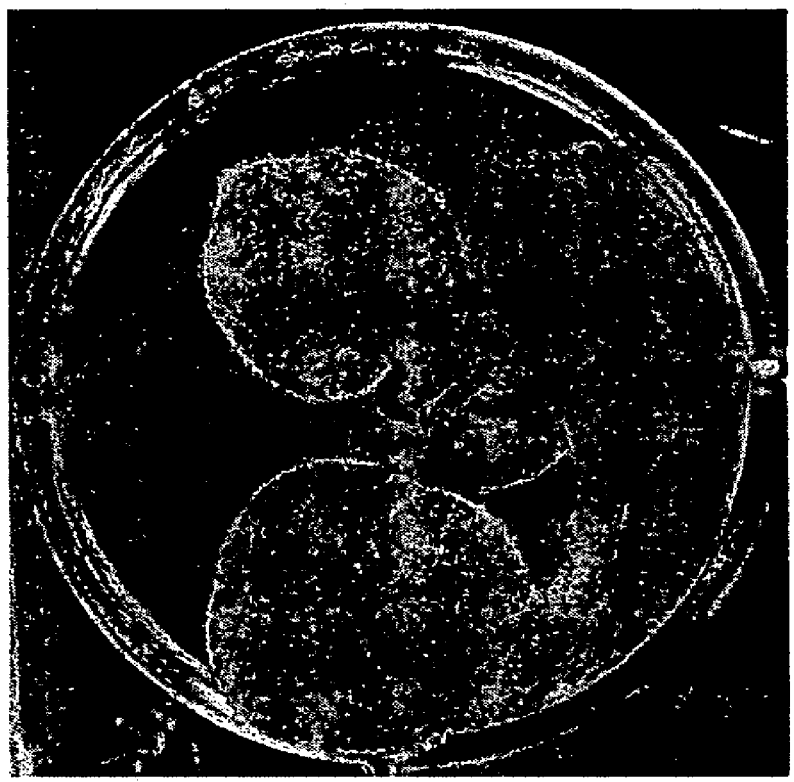
FIGS. 5A-C: Gene silencing in very young seedlings.
Figure 5A:
Figure 5B:
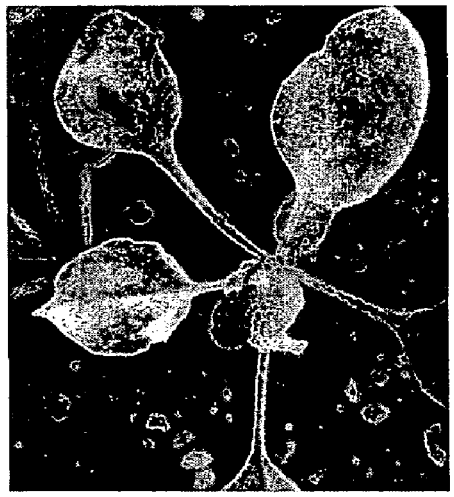
Figure 5B:
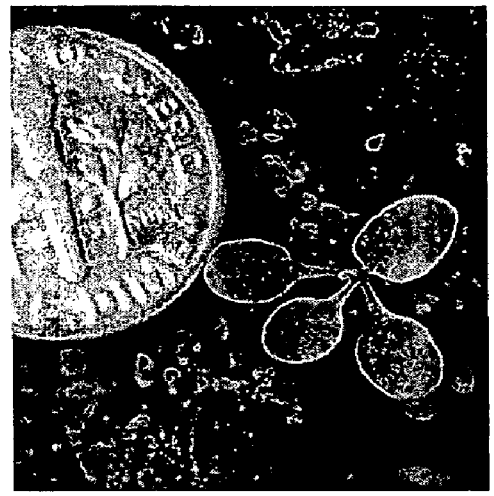
Figure 5B:
Figure 5B:
Figure 5C:
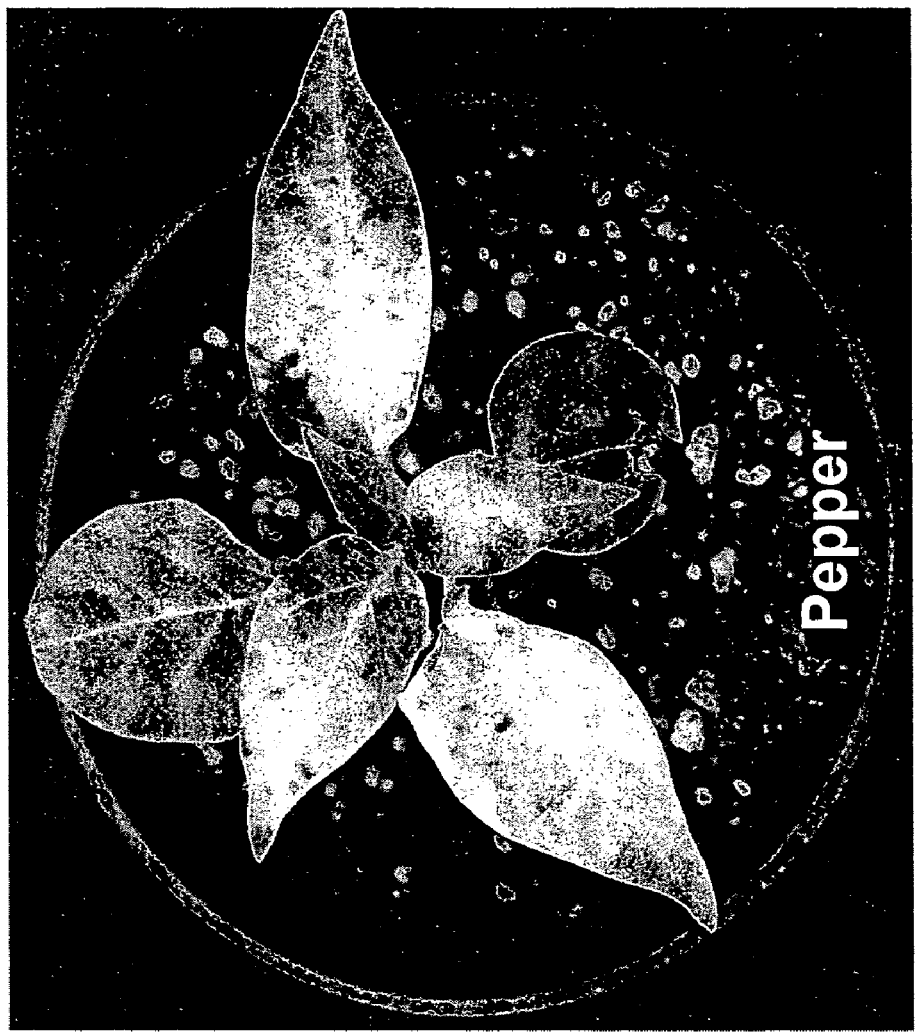
Figure 6:
FIG. 6: PDS silencing in Petunia. Petunia plant was inoculated with *Agrobacterium* containing TRV2-NbPDS by agrodrench method. Photograph was taken 21 days after inoculation.

*N. benthamiana* is a member of the Solanaceae, the nightshade family, a widely distributed group of plants to which many other economically important species also belong, including tomato, potato, pepper, eggplant, tobacco, and Petunia. Even though TRV can systemically move in many *Solanaceae* species, TRV-based VIGS has been demonstrated only in *N. benthamiana* and tomato (Ratcliff et al., 2001; Liu et al., 2002a and 2002b). The agrodrench method of VIGS was applied to different *Solanaceae* species such as tomato, tobacco, pepper, Petunia, potato, and eggplant using PDS and PB7 (encodes the β7 subunit of the 20S proteasome complex) as indicator genes. Using TRV2-NbPDS the inventors successfully silenced the endogenous PDS orthologs of tomato, tobacco, and Petunia, indicating that the PDS gene sequences are sufficiently conserved among these species to allow silencing (see FIG. 4A and FIG. 6). TRV2-NbPDS did not silence the PDS orthologs of pepper, potato and eggplant. To determine the efficiency of silencing in pepper, the PDS gene of pepper (pPDS) was then PCR amplified and cloned into the TRV2-VIGS vector by GATEWAY cloning (see EXAMPLE 1). TRV2-pPDS was able to successfully silence the endogenous pepper PDS by agrodrench method of inoculation (FIG. 4A). The relative abundance of PDS transcripts in the silenced plants was determined by semiquantitative RT-PCR (FIG. 4B). The primers used for RT-PCR were designed to specifically amplify transcripts of PDS orthologs in *N. benthamiana*, tomato, tobacco and pepper. Primers designed from tomato PDS (tPDS) gene sequence were able to amplify tPDS and PDS orthologs of *N. benthamiana* and tobacco. Separate pepper PDS gene specific primers were used to amplify pPDS. The PDS silencing was 100% efficient (as defined as the number of plants showing the silencing phenotype) on *N. benthamiana* while it was only around 60-70% efficient in other *Solanaceae* species tested by using agrodrench method of agroinoculation.

Figure 7:
FIG. 7: PB7 silencing in potato. Potato plant was inoculated with *Agrobacterium* containing TRV2-NbPB7 by agrodrench method. Photograph was taken 21 days after inoculation.
Figure 8:
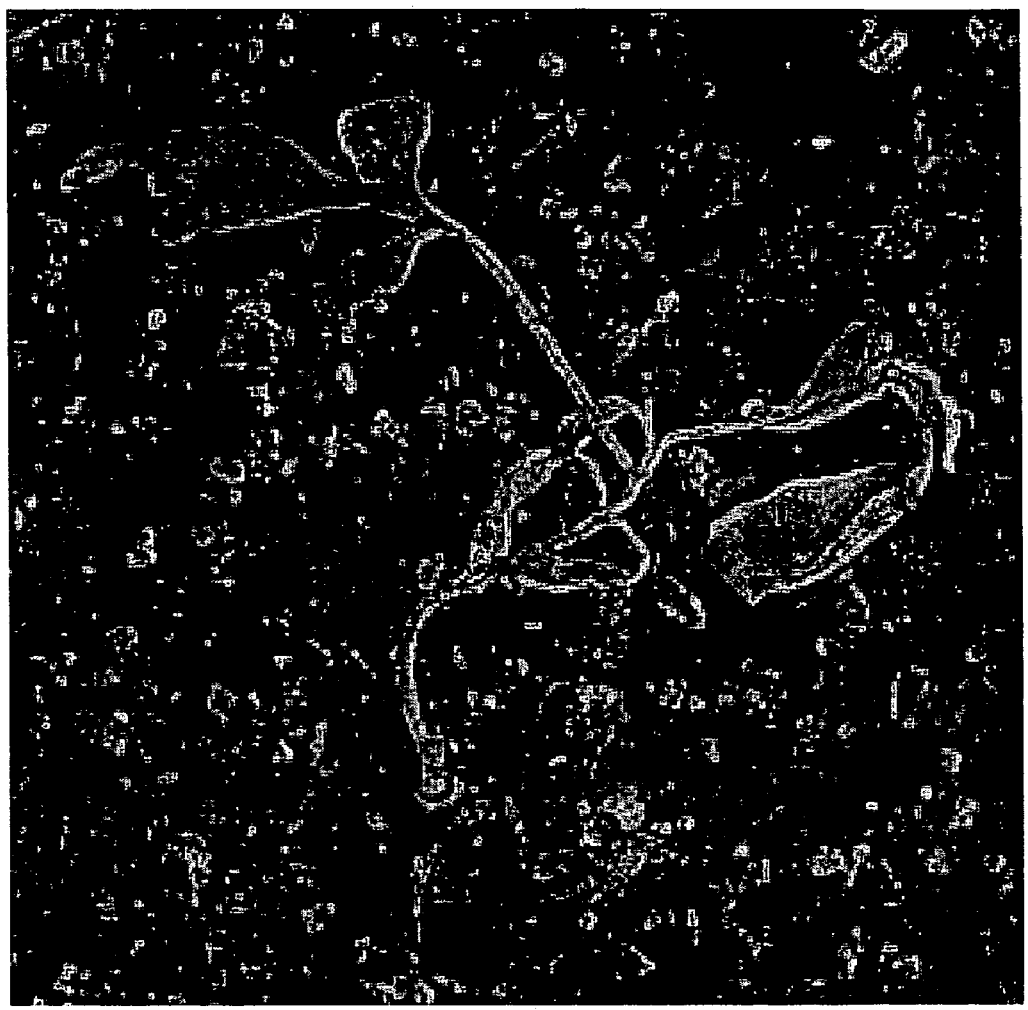
FIG. 8: Silencing of PB7 gene in soil grown tomato seedlings. Seeds were germinated in soil and one week after germination, *Agrobacterium* containing TRV2-NbPB7, along with *Agrobacterium* containing pTRV1, was applied by agrodrench method. One week after inoculation, cell death was observed in silenced plants. The photograph was taken 2 weeks after inoculation.

Silencing of PB7 produces systemic necrosis (spontaneous cell death) in *N. benthamiana* (Kim et al., 2003a and 2003b). PB7 was chosen as an indicator gene due to an obvious phenotype produced and that can be used to measure the efficacy of VIGS. A partial gene sequence of PB7 from *N. benthamiana* was cloned into TRV2-VIGS vector by GATEWAY cloning. TRV2-NbPB7 was inoculated by agrodrench onto above mentioned *Solanaceae* species. Two weeks after inoculation, a strong systemic necrosis phenotype was observed on *N. benthamiana*, tobacco, tomato, and pepper (FIG. 4A). Milder symptoms of the necrosis phenotype were observed on potato leaves (FIG. 7). The pattern of the cell death depended on plant species. *N. benthamiana* and tomato developed systemic necrosis in the meristem that progressed downwards, but tobacco and pepper showed severe symptoms on the stem and leaves while potato showed milder cell death on the leaves (FIG. 7). Interestingly the eggplant did not show a silencing phenotype with TRV2-NbPDS or TRV2-NbPB7 inoculations. It is possible that the eggplant PDS and PB7 gene sequences are more divergent compared to the other *Solanaceae* species tested. The PB7 silencing was more efficient (90 -100%) in producing visible symptoms when compared to PDS silencing in all the plants tested. It was proposed that PB7 silencing is a better visual indicator of VIGS when compared to PDS silencing.

The efficiency of the agrodrench method of VIGS was compared with the leaf infiltration method of VIGS in various *Solanaceae* species. In tomato (Rutgers cultivar), the efficiency of VIGS by the agrodrench method was significantly higher than by leaf infiltration. Recently, it has been shown that the vacuum infiltration of the entire seedlings with *Agrobacterium* containing TRV-VIGS vectors is more efficient in gene silencing for the Rio-Grande cultivar of tomato when compared to spraying or syringe infiltration of individual leaves (Ekengren et al., 2003). However, even though the vacuum infiltration method can be efficient, it can be laborious to do VIGS in a high throughput manner. Further, no significant differences were observed in the efficiency of VIGS between agrodrench and leaf infiltration methods for *N. benthamiana*, tobacco, pepper and Petunia. These data therefore indicate that agrodrench is a simple and highly effective method for VIGS in various *Solanaceae* and other species.

EXAMPLE 5

Agrodrench is Effective to Elicit VIGS in Very Young Seedlings

One of the advantages of VIGS is that it can be applied to mature plants to assess function for genes, whose mutation (or antisensing) might be lethal in sexually propagated plants (Baulcombe, 1999). However, current VIGS protocols are limited in assessing function of genes in young seedlings or during seedling development. The leaf infiltration method of VIGS is normally applied to 3-4 week old seedlings having at least two true leaves. Maximum gene silencing is normally observed 2 weeks after agroinoculation and by that time the age of the plant is at least 5-6 weeks. In contrast, the agrodrench method of VIGS was used to silence specific genes in 1-2 week old young seedlings. PDS, PB7 and Chl H genes were used as visual indicators of gene silencing. Chl H encodes the H subunit of magnesium protoporphyrin chelatase, an enzyme involved in chlorophyll biosynthesis, popularly known as the sulphur (Su) gene (Hiriart et al., 2002 and 2003). Reduction or absence of magnesium protoporphyrin chelatase in plants will result in yellow colored leaves due to reduction in chlorophyll synthesis. Occurrence of the visual phenotype of Chl H silencing was much faster than PDS silencing in *N. benthamiana*. Therefore Chl H silencing was more sensitive and a better visual indicator of gene silencing than PDS silencing and hence Chl H was used as one of the indicators for gene silencing in young seedlings.

The *N. benthamiana* Chl H gene was PCR amplified from *N. benthamiana* leaf cDNA and cloned into a TRV2-VIGS vector by GATEWAY cloning, in a similar fashion as was done with PDS and PB7. Agrodrench method was used to individually inoculate *Agrobacterium* strains containing either TRV2-NbChl H or TRV2-NbPDS or TRV2-NbPB7 on freshly germinated one week old soil grown seedlings of *N. benthamiana*, pepper, Petunia and tomato. The agrodrench method of agroinoculation was also applied to plants grown under sterile condition. *Agrobacterium* strains containing either TRV2-NbChl H or TRV2-NbPDS were inoculated, by dropping 50 µl of bacterial suspension at the crown part of the one week old seedling on the sterile media on which *N. benthamiana* seedlings were germinated. Seven to ten days after inoculation, yellowing, photobleaching and cell death phenotypes were observed for plants inoculated with TRV2-NbChl H, TRV2-NbPDS and TRV2-NbPB7 respectively (FIGS. 5A-C and FIG. 8). Interestingly, application of agrodrench directly to seeds or germinating seeds failed to elicit VIGS. The minimum age at which agrodrench achieved gene silencing in these studies was one week. These results indicate that agrodrench is an effective method to do VIGS in very young seedlings. Agrodrench method of VIGS in very young seedlings will open a new research area to study the role of certain genes during seedling development in both soil and sterile system.

Agrodrench overcomes limitations of conventional leaf infiltration methods of agroinoculation that cannot be applied to certain plants or very young seedlings. Additionally, the ease of the agrodrench indicates that it would be a better choice for high-throughput gene silencing than leaf infiltration. Agrodrench is efficient for VIGS in various *Solanaceae* species and in tomato agrodrench was indicated to be more efficient in eliciting VIGS when compared to leaf infiltration. The effectiveness of agrodrench was demonstrated using PDS, PB7 and Chl H genes as indicators of gene silencing in foliar tissue. PB7 and Chl H are more sensitive indicators of gene silencing than PDS. The above examples also demonstrate that VIGS can be successfully used to silence genes in roots, and the agrodrench method is more effective than the leaf infiltration method for VIGS in roots. Thus agrodrench may also find use in gene functional analyses during symbiotic interactions such as plant-*Rhizobium* and plant-mycorrhizal symbiosis.

EXAMPLE 6

Agrodrench can be Utilized for Large Scale VIGS Experiments Using a Fast-forward Genetics Approach.

Figure 2:
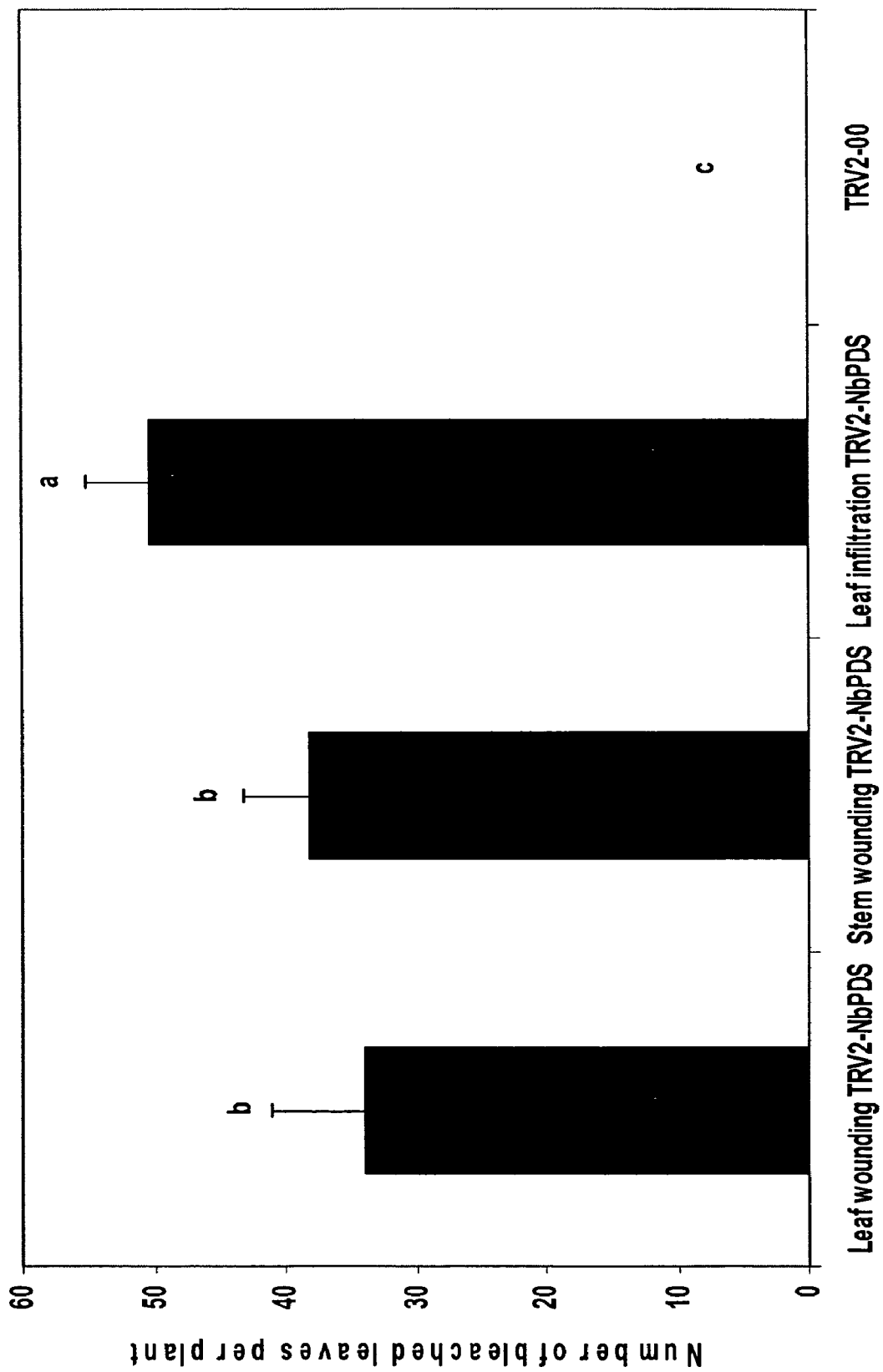
FIG. 2: Feasibility of using agrodrench for large scale experiments. *N. benthamiana* plants were inoculated with *Agrobacterium* containing pTRV1 by agrodrench method. One week after TRV1 inoculation, *Agrobacterium* containing pTRV2 alone (TRV2::00) or TRV2-NbPDS was inoculated either by wounding the stem or leaf with toothpick or infiltrating the leaf with a needle-less syringe. Number of bleached leaves per plant in each treatment was counted 21 days after TRV2 inoculation. Letters indicate significant differences using Fisher's LSD test at P=0.05.

VIGS is an effective tool for high throughput fast-forward genetics (Baulcombe, 1999). Using this approach it was recently shown that a heat shock protein 90 plays a critical role in plant disease resistance (Lu et al., 2003b). However, fast-forward genetics using TRV vectors normally involves infiltrating freshly grown *Agrobacterium* strain containing TRV1, using a needle-less syringe, to leaves of 3-4 week old *N. benthamiana* plants. Clones from 96-well plates containing TRV2 (contains cDNA library) can be individually picked with a tooth pick and can be pricked to the area of the leaf infiltrated with TRV1. Leaf infiltration of TRV1 to hundreds of plants can be very laborious. To demonstrate ease of use, the agrodrench method was used to apply TRV1 to *N. benthamiana* plants. TRV1 alone, in the absence of TRV2, has been previously shown to move systemically in plants (Ratcliff et al., 2001). One week after TRV1 application, *Agrobacterium* (grown on solid medium) containing TRV2-NbPDS was picked with a toothpick and inoculated on to either the stem or leaf of *N. benthamiana* plants. Liquid grown *Agrobacterium* containing TRV2-NbPDS was also applied by the leaf infiltration method. Photobleaching was observed on the upper leaves of all the plants inoculated with TRV2-NbPDS (FIG. 2). These results indicate that the agrodrench method can be effectively used for high throughput TRV-vector based VIGS experiments, thereby minimizing the labor needed for such studies.

All of the compositions and methods disclosed and claimed herein can be made and executed without undue experimentation in light of the present disclosure. While the compositions and methods of this invention have been described in terms of preferred embodiments, it will be apparent to those of skill in the art that variations may be applied to the compositions and methods and in the steps or in the sequence of steps of the methods described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The references listed below are incorporated herein by reference to the extent that they supplement, explain, provide a background for, or teach methodology, techniques, and/or compositions employed herein.

U.S. Pat. No. 4,237,224
U.S. Pat. No. 4,264,731
U.S. Pat. No. 4,273,875
U.S. Pat. No. 4,322,499
U.S. Pat. No. 4,336,336
Abbink et al., *Virology*, 295:307-319, 2002.
Agrios, In: *Plant Pathology*, 4$^{th}$ Ed., San Diego, Academic Press, 1997.
Baulcombe, *Arch. Virol.*, (15):189-201, 1999.
Baulcombe, *Current Biol.*, 12:R82-R84, 2002
Brigneti et al., *EMBO J.*, 17:6739-6746, 1998.
Burger et al., *J. Exp. Bot.*, 54:1675-1683, 2003.
Burr and Otten, *Annu. Rev. Phytopathol.*, 37:53-80, 1999.
Burton et al., *Plant Cell*, 12(5):691-706, 2000.
Dinesh-Kumar et al., In: *Plant Functional Genomics*, Grotewold (Ed.), Humana Press, Inc., Totowa, N.J., 236:287-293, 2003.
Ekengren et al., *Plant J.*, 36:905-917, 2003.
Escobar and Dandekar, *Trends Plant Sci.*, 8, 380-386, 2003.
Evans and Jeske, *Virology*, 197:492-496, 1993.
Goodwin et al., *Plant Cell*, 8, 95-105, 1996.
Gosselé et al., *Plant J.*, 32:859-866, 2002.
Guo and Ding, *EMBO J.*, 21:398-407, 2002.
Guo and Garcia, *Mol. Plant-Microbe Interact.*, 10,160-170, 1997.
Hanley-Bowdoin et al., *Nucleic Acids Res.*, 25:10511-10528, 1988.
Hiriart et al., *Mol. Plant-Microbe Interact.*, 16:99-106, 2003.
Hiriart et al., *Plant Mol. Biol.*, 50:213-224, 2002.
Holzberg et al., *Plant J.*, 30:315-327, 2002.
Kim et al., *J. Biol. Chem.*, 278:19406-19415, 2003b.
Kim et al., *Mol. Cells*, 15:127-132, 2003a.
Kumagai et al, *Proc. Natl. Acad. Sci. USA*, 92,1679-1 683, 1995.
Lindbo et al, *Plant Cell* 5, 1749-1 759, 1993.
Liu et al., *Plant J.*, 30:415-429, 2002b.
Liu et al., *Plant J.*, 31:777-786, 2002a.
Lu et al., *EMBO J.*, 22:5690-5699, 2003.
Lu et al., *Methods*, 30:296-303, 2003.
MacFarlane and Popovich, *Virology*, 267:29-35, 2000.
Matthews, In: *Plant Virology*, 3$^{rd}$ Ed., San Diego,:Academic Press, 1991.
Peart et al., *Proc. Natl. Acad. Sci. USA*, 99:10865-10869, 2002.
Peele et al., *Plant J.*, 27(4):357-366, 2001.
Pruss et al, *Plant Cell*, 859-868, 1997.
Ratcliff et al., *Plant J.*, 25:237-245, 2001.
Rochester et al., *Virology*, 178:520-526, 1990.
Ruiz et al., *Plant Cell*, 10:937-946, 1998.
Saedler and Baldwin, *J. Exp. Bot.*, 55:151-157, 2003.
Sharma et al., *Mol. Genet. Genomics*, 269:583-591, 2003.
Smith et al, *Plant Cell*, 6,1441-1453, 1994.
Vance and Vautheret, *Science*, 292(5525):2277-2280, 2001.
Vellios et al., *Virology*, 15:118-124, 2002.
Visser and Bol, *J. Gen. Virol.*, 80:3273-3280, 1999.
Visser et al., *Virology*, 263:155-165, 1999.
Voinnet, *Trends Genet.*, 17:449-459, 2002.
Yoshioka et al., *Plant Cell*, 15:706-718, 2003.

What is claimed is:

1. A method of inhibiting the expression of a plant gene in a plant comprising the steps of:
   a) obtaining a solution comprising recombinant *Agrobacterium tumefaciens* comprising a vector comprising a heterologous nucleic acid sequence complementary to the plant gene or the complement thereof and a nucleic acid sequence of a virus, wherein the vector induces virus-induced gene silencing of said plant gene; and
   b) contacting roots of the plant with the solution, wherein the expression of the plant gene is inhibited in the plant.

2. The method of claim 1, wherein the heterologous nucleic acid sequence is in sense orientation.

3. The method of claim 1, wherein the heterologous nucleic acid sequence is in antisense orientation.

4. The method of claim 1, wherein the heterologous nucleic acid sequence is in sense and antisense orientation.

5. The method of claim 1, wherein contacting the roots of the plant with the solution is carried out when the plant is from about 1 to about 3 weeks of age.

6. The method of claim 1, wherein the heterologous nucleic acid sequence comprises at least 25 nucleotides complementary to said target plant gene.

7. The method of claim 1, wherein the heterologous nucleic acid sequence comprises at least 75 nucleotides complementary to said target plant gene.

8. The method of claim 1, wherein the heterologous nucleic acid sequence comprises a cDNA from the target plant gene or a fragment thereof.

9. The method of claim 1, wherein the plant is a dicotyledonous plant.

10. The method of claim 9, wherein the dicotyledonous plant is tobacco or tomato.

11. The method of claim 9, wherein the dicotyledonous plant is soybean, alfalfa, cotton, peanut or pea.

12. The method of claim 9, wherein the plant is a member of the family Solenaceae.

13. The method of claim 12, wherein the plant is tomato, pepper or tobacco.

14. The method of claim 1, wherein the plant is a monocotyledonous plant.

15. The method of claim 14, wherein the monocotyledonous plant is wheat, maize, rye, rice, oat, barley, turfgrass, sorghum, millet or sugarcane.

16. The method of claim 1, wherein the virus is selected from the group consisting of Tobacco rattle virus (TRV) and Potato virus X (PVX).

17. The method of claim 1, wherein said plant is in a growth media.

18. The method of claim 17, wherein the growth media is soil or agar.

19. The method of claim 1, wherein the expression of the target gene is inhibited in the roots of the plant.

20. The method of claim 1, wherein the expression of the target gene is inhibited in leaves or stems of the plant.

21. The method of claim 17, wherein step b) comprises applying the solution to the growth media.

22. A method of identifying a phenotypic change resulting from a decrease in expression of a plant gene, the method comprising the steps of:
   a) obtaining a solution comprising recombinant *Agrobacterium tumefaciens* comprising a vector comprising a heterologous nucleic acid sequence complementary to the plant gene or the complement thereof and a nucleic acid sequence of a virus, wherein the vector is capable of inducing virus-induced gene silencing of said plant gene; and
   b) contacting the roots of a plant with said solution, wherein the expression of the plant gene is inhibited in the plant; and
   c) identifying a phenotypic change associated with the plant gene based on a difference in the phenotype of the plant relative to a corresponding plant which has not been contacted with the solution.

23. The method of claim 22, wherein step b) is performed on a population of plants.

24. The method of claim 23, wherein the solution in step b) comprises a population of recombinant *Agrobacterium tumefaciens* comprising a plurality of heterologous nucleic acid sequences.

25. The method of claim 22, wherein the plant is a monocotyledonous plant.

26. The method of claim 25, wherein the plant is rice.

27. The method of claim 22, wherein the plant is a dicotyledonous plant.

28. The method of claim 22, wherein the plant is a member of the family Solenaceae.

29. The method of claim 28, wherein the plant is tomato, pepper or tobacco.

30. The method of claim 22, wherein the virus is selected from the group consisting of Tobacco rattle virus (TRV) and Potato virus X (PVX).

31. The method of claim 22, wherein identifying an altered phenotype comprises a chemical assay or visual observation.

32. The method of claim 22, wherein the expression of the plant gene is inhibited in roots, leaves or stems of the plant.

33. A high-throughput method for identifying a phenotypic change resulting from a decrease in expression of a plant gene, the method comprising the steps of:
   a) obtaining:
      i) a plurality of solutions each comprising recombinant *Agrobacterium tumefaciens* comprising a vector comprising a heterologous nucleic acid sequence complementary to a plant gene or the complement thereof and a nucleic acid sequence of a virus, wherein the vector induces virus-induced gene silencing in said plant, wherein the recombinant *Agrobacterium tumefaciens* collectively comprise heterologous nucleic acid sequences complementary to a plurality of plant genes or the complements thereof and
      ii) a population of plants the roots of which are comprised in a growth media;
   b) contacting the roots of the members of the population of plants with at least one solution from said plurality of solutions wherein the expression of at least one gene from the plurality of plant genes is inhibited in the population of plants and wherein all members of the population are not contacted with the same solutions; and
   c) identifying a phenotypic change resulting from a decrease in expression of the plant gene from the population of plants based on a change in the phenotype of at least one plant contacted with the recombinant *Agrobacterium tumefaciens* relative to a plant that has not been contacted with the recombinant *Agrobacterium tumefaciens*.

* * * * *

SEQUENCE LISTING

<160> NUMBER OF SEQ ID NOS: 18

<210> SEQ ID NO 1
<211> LENGTH: 49
<212> TYPE: DNA
<213> ORGANISM: Artificial Sequence
<220> FEATURE:
<223> OTHER INFORMATION: Description of Artificial Sequence: Synthetic Primer

<400> SEQUENCE: 1
ggggacaagt ttgtacaaaa aagcaggctg caatggaagg aacattcga            49

```
<210> SEQ ID NO 2
<211> LENGTH: 49
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 2
ggggaccact ttgtacaaga aagctgggta gtctctcagg aggattacc                49

<210> SEQ ID NO 3
<211> LENGTH: 49
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 3
ggggacaagt ttgtacaaaa aagcaggctc ttttcactgg agttgtccc                49

<210> SEQ ID NO 4
<211> LENGTH: 48
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 4
ggggaccact ttgtacaaga aagctgggtg cttgtcggcc atgatgta                 48

<210> SEQ ID NO 5
<211> LENGTH: 56
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 5
ggacaagttt gtacaaaaaa gcaggctcga gcggccgccc gggcaggtgg agatgt        56

<210> SEQ ID NO 6
<211> LENGTH: 59
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 6
ggggaccact ttgtacaaga aagctgggtc atgaatttga gcttgaaact tgccattgt     59

<210> SEQ ID NO 7
<211> LENGTH: 21
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 7
cacagagcgt ggttactcat c                                              21
```

```
<210> SEQ ID NO 8
<211> LENGTH: 22
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 8
gcaatacctg ggaacatggt ag                                              22

<210> SEQ ID NO 9
<211> LENGTH: 20
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 9
cctgcagaag agtgggtatc                                                 20

<210> SEQ ID NO 10
<211> LENGTH: 20
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 10
gtataggagc ttgtcccctg                                                 20

<210> SEQ ID NO 11
<211> LENGTH: 17
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 11
gctcactgct cagtgtg                                                    17

<210> SEQ ID NO 12
<211> LENGTH: 17
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 12
cgcttgcttc cgacaac                                                    17

<210> SEQ ID NO 13
<211> LENGTH: 20
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 13
cttttcactg gagttgtccc                                                 20

<210> SEQ ID NO 14
```

```
<211> LENGTH: 19
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 14
gcttgtcggc catgatgta                                                 19

<210> SEQ ID NO 15
<211> LENGTH: 27
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 15
tggtgtcctc aagcctggta tggttgt                                        27

<210> SEQ ID NO 16
<211> LENGTH: 30
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 16
acgcttgaga tccttaaccg caacattctt                                     30

<210> SEQ ID NO 17
<211> LENGTH: 24
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 17
ctgggttact agcggcactg aata                                           24

<210> SEQ ID NO 18
<211> LENGTH: 24
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 18
tccaccaaac ttaatcccga atac                                           24
```